United States Patent [19]

Morris

[11] Patent Number: 5,116,981

[45] Date of Patent: May 26, 1992

[54] ANTIINFLAMMATORY LEUKOTRIENE B₄ ANALOGS

[75] Inventor: Joel Morris, Kalamazoo, Mich.

[73] Assignee: The Upjohn Company, Kalamazoo, Mich.

[21] Appl. No.: 438,491

[22] PCT Filed: Dec. 22, 1987

[86] PCT No.: PCT/US87/03364

§ 371 Date: Jun. 29, 1989

§ 102(e) Date: Jun. 29, 1989

[87] PCT Pub. No.: WO88/05045

PCT Pub. Date: Jul. 14, 1988

Related U.S. Application Data

[63] Continuation-in-part of Ser. No. 947,018, Dec. 29, 1986, abandoned.

[51] Int. Cl.⁵ .............. C07D 213/55; C07D 307/46; C07D 405/06; C07C 33/28; A61K 31/045; A61K 31/19; A61K 31/335; A61K 31/44

[52] U.S. Cl. .................... 546/268; 546/283; 546/335; 546/336; 546/341; 546/342; 546/344; 549/273; 549/320; 549/323; 549/497; 549/499; 549/502; 549/554; 549/561; 560/60; 562/426; 562/470; 568/715; 568/807; 568/811; 568/812; 568/813; 514/277; 514/336; 514/357; 514/451; 514/461; 514/471; 514/475; 514/532; 514/533; 514/559; 514/562; 514/570

[58] Field of Search .............. 549/499, 273, 320, 502; 546/268, 301, 283, 335, 336, 341, 342, 344; 560/55, 60; 562/465, 470, 496, 426; 568/813, 715, 807, 811, 812; 514/315, 461, 532, 559, 568, 438, 570, 277, 336, 357, 451, 471, 475, 533, 562

[56] References Cited

U.S. PATENT DOCUMENTS 3,954,813  5/1976  Nedenskov et al. .............. 549/499
4,791,133 12/1988  Djuric et al. ...................... 514/438
4,855,324  8/1989  Djuric et al. ...................... 514/570

FOREIGN PATENT DOCUMENTS 0029247 5/1981  European Pat. Off. ............. 549/499
0142145 5/1985  European Pat. Off. ............. 549/499
0194093 9/1986  European Pat. Off. ............. 549/499

OTHER PUBLICATIONS

Jun. 1, 1984, Japan (Chem. Abstracts 101:23022q), Tokkyo.
Aug. 20, 1982, Japan (Derwent Abstract only 84-084453) Ono I.
Nov. 24, 1982, Japan (Derwent Abstract only 84-173740), Ono II.
Nov. 19, 1984, Europe (Derwent Abstract 86-145415), Sumitomo.
Corey, et al. I, Advances in Prostaglandin and Thromboxane Research, vol. 6, 19-25, (1980).
Corey, et al. II, Tetrahedron Letters, 4243-4246, (1980).
Cromwell, et al., The Lancet, Jul. 25, 164-165, (1981).
Dahlén, Nature, vol. 288, 484-486, (1980).
Goetzl, et al., Journal of Clinical Immunology, 79-84 (1984).
Namiki, et al., Biochemical and Biophysical Research Communications, 540-546 (1986).
Samuelsson, et al., Advances in Prostaglandin and Thromboxane Research, vol. 6, 1-18, (1980).
Samuelsson, Science, vol. 220, 568-575, (1983).
Chemical Abstracts, vol. 101, No. 25, #230231j, Dec. 17, 1984, Ikegami et al.
Salomon, R. G., Accounts of Chemical Research, vol. 18, No. 10, Oct. 1985, pp. 294-301, "Prostaglandin Endoperoxide Reaction Mechanisms and the Discovery of Levuglandins".

Primary Examiner—Mary C. Lee
Assistant Examiner—Fiona T. Powers
Attorney, Agent, or Firm—D. L. Corneglio

[57] ABSTRACT

This invention encompasses novel analogs of Leukotriene B₄ which are selected from a compound of formula I, $B-C\approx C-CH_2C(M_2)-C\approx C-Y-C(M_1)-A$, or formula II, $B-C\approx C-CH_2C(M_2)-C\approx C-P-R_5-A$: wherein Y is:

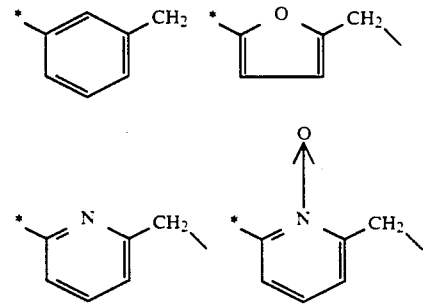

wherein P is:

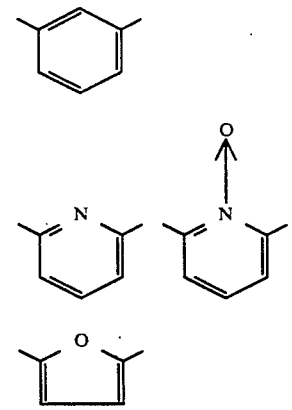

Patentable intermediates, process for making the novel analogs and intermediates and preparation of useful pharmacological agents comprising the analogs and intermediates are part of this invention.

8 Claims, No Drawings

ANTIINFLAMMATORY LEUKOTRIENE B$_4$ ANALOGS

CROSS-REFERENCE TO RELATED APPLICATIONS

This application corresponds to PCT patent application PCT/US87/03364 filed Dec. 22, 1987, which was a continuation-in-part of U.S. Ser. No. 947,018 filed Dec. 29, 1986, abandoned.

BACKGROUND OF THE INVENTION

Metabolites of arachidonic acid constitute a class of important biological compounds. Members of this class include prostaglandins, prostacyclins, thromboxanes, and leukotrienes.

The leukotrienes are recent additions to this family of biologically important compounds. The leukotrienes are unsaturated fatty acid compounds derived from arachidonic acid by the action of lipoxygenase. Pioneering work in the isolation and identification of leukotrienes was reported at the Fourth International Prostaglandin Conference in 1979 by Samuelsson, et al., Leukotrienes: A New Group of Biologically Active Compounds, *Advances in Prostaglandin and Thromboxane Research*, Vol. 6, 1–18, (1980). Early synthetic work in the field was presented at the same conference by Corey, et al., Recent Studies on the Chemical Synthesis of Eicosanoids, *Advances in Prostaglandin and Thromboxane Research*, Vol. 6, 19–25, (1980). The leukotrienes constitute a general biological control system based on the precursor molecule arachidonic acid. Arachidonic acid is normally stored in biological membrane structures and can be released through activation of a hydrolytic system by a variety of stimuli. Depending on the availability of active enzymes in the stimulated cell, arachidonic acid transforms into one or several biologically active compounds. A variety of stimuli can thus be converted into a multitude of compounds that can regulate or mediate various cell functions. The new knowledge about this system suggests new possibilities for the development of novel and more specific therapeutic agents, particularly in diseases related to immediate hypersensitivity reactions and inflammation. Such drugs might be based on antagonism of end products or inhibition of enzymes involved in the generation and further transformation of key intermediates, Samuelsson, Leukotrienes: Mediators of Immediate Hypersensitivity Reactions and inflammation, *Science*, Vol. 220, 568–575, (1983).

Continuing work has shown the leukotrienes are important in the cellular regulation of diverse functions. LTB$_4$, itself, stimulates aggregation and degranulation of human neutrophils, promotes chemotaxis and chemokinesis of leukocytes, mediates lysosomal enzyme release and superoxide generation and constricts respiratory smooth muscle through an indirect mechanism involving stimulation of the release of cycloxygenase products. LTB$_4$ is implicated in cystic fibrosis, asthma, adult respiratory distress syndrome, cutaneous allergic reactions, spondyloarthritis, rheumatoid arthritis, gout and inflammatory bowel disease because elevated concentrations of LTB$_4$ have been found in sputum, lung edema fluid, epidermis, skin chamber fluid, synovial fluid and mucosa, Goetzl, et al., *Journal of Clinical Immunology*, 82, (1984). The known effects of LTB$_4$ indicate agonists or antagonists would be useful in many physiological conditions. For example, an LTB$_4$ antagonist would be useful in the treatment of inflammatory conditions where it is desirable to prevent migration of polymorphonuclear leukocytes to the inflammatory site. An LTB$_4$ antagonist would also be useful in the treatment of respiratory diseases associated with hypersensitivity because the leukotrienes are potent constrictors of human bronchi, Dahlén, *Nature*, Vol. 288, 484, (1980). As noted, LTB$_4$ is found in the sputum of cystic fibrosis patients, Cromwell, et al., *The Lancet*, July 25, 164–165, (1981), suggesting the leukotrienes contribute to the rate of mucous secretions in the human respiratory tract. The excessive production of mucus, however, is a symptom of many pulmonary diseases. For example, in chronic bronchitis the flow of mucus may increase up to four times the normal rate. The inability of the patient to deal with this hyper-production causes conditions such as chronic bronchitis, asthma, and cystic fibrosis.

The role of leukotrienes as agonists in immediate hypersensitivity and other pathological conditions has led to research into inhibitors of leukotriene biosynthesis and leukotriene antagonists, Corey, et al., *Tetrahedron Letters*, 4243, (1980). Receptors for LTB$_4$ have been characterized in human neutrophils and HL-60 cells. Although many compounds are known which interfere with the biosynthesis of LTB$_4$, relatively few agents have been prepared which directly block its pharmacological effects. LTB$_4$ diacetate has been reported to competitively inhibit chemotactic response of equimolar concentrations of LTB$_4$. The corresponding dimethylamide of LTB$_4$ is reported to inhibit neutrophil degranulation induced by LTB$_4$ at concentrations where the agent has no appreciable agonist activity.

INFORMATION DISCLOSURE

Documents referring to compounds as anti-leukotriene B$_4$ agents, leukotriene B$_4$ related compounds, leukotriene B$_4$ analogs, leukotriene B$_4$ compounds, or LTB$_4$-antagonist include: 1) Namiki, et al., Pharmacological Profiles of a Potential LTB4-Antagonist, SM-9064, *Biochemical and Biophysical Research Communications*, 540–546 (1986); 2) New dihydroxyalkenoic acids, ester(s) and amide(s)—useful as potent antileukotriene B4 agents for use against inflammation and allergies, Derwent, 86-145415; 3) Leukotriene B4—related compounds, Chem Abstracts, 101:23022q; 4) Leukotriene B4 analogs—useful as antiinflammatory and antiallergic agents, Derwent, 84-173740; 5) Leukotriene B4 compound for antiinflammatory and antiallergic drugs—specifically (5RS)-6,7-dihydro-5,8-ethano-13,14,15,16,17,18,19,20-octanol LTB4, Derwent, 84-084453. These documents disclose compounds with general biological activities similar to the compounds of this invention but which are structurally different from the compounds of this invention.

FIELD OF INVENTION

The present invention encompasses pharmaceutically useful compounds which are novel analogs of Leukotriene B$_4$.

SUMMARY OF INVENTION

This invention teaches LTB$_4$ analogs of a compound of formula I, B—C$\simeq$C—CH$_2$C(M$_2$)—C$\simeq$C—Y—C(M$_1$)—A or formula II, B—C$\simeq$C—CH$_2$C(M$_2$)—C$\simeq$C—P—R$_5$—A:

wherein Y is as defined in Chart A, formulae A-1-A4
wherein P is as defined in Chart A, formulae A-5-A-8
wherein A is —CH$_2$CH$_2$CH$_2$Z;
wherein Z is
- (a) —CO$_2$L$_5$,
- (c) —CH$_2$OH,
- (h) —CH$_3$, wherein L$_5$ is
- (a) hydrogen,
- (b) (C$_1$-C$_{12}$) alkyl,
- (c) (C$_3$-C$_{10}$) cycloalkyl, wherein B is —C(M$_3$)—R$_2$;
wherein M$_3$ is
- (a) α-R$_3$,β-R$_4$,
- (b) α-R$_4$,β-R$_3$, or
- (c) a mixture of α-R$_3$,β-R$_4$, and α-R$_4$,β-R$_3$;

wherein R$_3$ and R$_4$ are the same or different and are
- (a) hydrogen,
- (b) fluorine or
- (c) CH$_3$;

with the proviso that one of R$_3$ and R$_4$ is fluorine only when the other of R$_3$ and R$_4$ is hydrogen or fluorine;

wherein R$_2$ is
- (a) hydrogen,
- (b) —(CH$_2$)$_a$CH$_3$ wherein a is an integer of from 1 to 5, wherein —C(M$_3$)—R$_2$ taken together is
- (a) (C$_4$-C$_7$) cycloalkyl wherein R$_5$ is
- (a) cis —CH=CH—,
- (b) trans —CH=CH—,
- (c) —C≡C—,
- (d) —C(M$_4$)—C(M$_1$)—,
- (e) —CH(R$_6$)—C(M$_1$)—,
- (f) —C(M$_4$)—Z$_1$,
- (g)

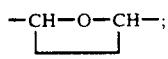

wherein M$_1$, M$_2$ and M$_4$ are the same or different and are
- (a) αOL$_p$,βhydrogen,
- (b) βOL$_p$,αhydrogen,
- (c) a mixture of αOL$_p$,βH and βOL$_p$,αhydrogen,
- (d) αOL$_p$,βCH$_3$,
- (e) βOL$_p$,αCH$_3$,
- (f) a mixture of αOL$_p$,βOL$_p$ and βOL$_p$,αCH$_3$, with the proviso that both M$_1$ and M$_4$ are not =O and with the proviso that M$_4$ is not hydrogen,hydrogen;

wherein L$_p$ is hydrogen or a hydroxyl protective group;
wherein M$_1$ and A taken together are a 5 or 6 membered lactone or lactol,
wherein R$_6$ is
- (a) —SL$_7$, wherein Z$_1$ is a 5 or 6 membered lactone or lactol;
wherein L$_7$ is
- (a) —(CH$_2$)$_2$CO$_2$H,
- (b) —CH$_2$CO$_2$H,
- (c) —CH$_2$CH(NH$_2$)CO$_2$H,
- (d)

- (e) —(C$_6$H$_4$)(R$_7$)(R$_8$);

wherein the use of the symbol, *, in the formulas indicates the site of attachment of the side chain containing the group B. The unmarked site indicates the site of attachment containing the group A. If neither site is marked, the side chains can be attached in either orientation provided one side chain contains the group B and the other side chain contains the group A.

This invention also includes the pharmacologically acceptable salts of compounds of formulas I and II, any reference to formulas I or II includes salts of the appropriate compounds defined thereby.

DETAILED DESCRIPTION OF INVENTION

The compounds of the present invention will be named herein using the Chemical Abstracts numbering system (see Naming and Indexing of Chemical Substances for Chemical Abstracts during the Ninth Collective Period (1972-1976), a reprint of section IV from the Volume 76 Index Guide.) For a discussion of leukotriene nomenclature, see Samuelsson, et al., *Prostaglandins*, Vol. 19, 645 (1980).

The use of the symbol, ~, in the formulas represents —CH$_2$CH$_2$—, cis or trans —CH=CH—, or a mixture of cis and trans —CH=CH— and the symbol, ≈, in the formulas represents —CH$_2$CH$_2$—, cis or trans —CH=CH—, a mixture of cis and trans —CH=CH—, or —C≡C—.

Stereochemistry is represented in the formulas according to the following conventions: When a formula is written in its extended linear form, substituents below the plane of the aromatic ring are designated α and are represented by broken line attachments. Substituents above the plane of the aromatic ring are designated β and are represented by heavy solid line attachments. Substituents either below or above the plane of the aromatic ring and/or mixtures of α and β are represented by wavy line attachments. If no stereochemistry is indicated, the configuration of the substituent is α, β or a mixture of α and β.

The compounds of this invention each have several centers of asymmetry. Preparation of these compounds can give, therefore, optically pure compounds (a single enantiomer), optically inactive compounds (equal numbers of both enantiomers), a partially enriched mixture (unequal numbers of both enantiomers) or a mixture of diastereomers (more than 1 pair of enantiomers). The formulas used herein are intended to represent all possible diastereomers. A formula representing a single enantiomer will be indicated by the prefix; (opt. act.). A racemic mixture will be indicated by the prefix; (±).

Generic substituents bonded to carbon are designated as R$_i$, where i is an integer. Generic substituents bonded to atoms other than carbon are designated L$_i$, where i is an integer. Hydroxyl protecting groups are designated L$_p$, when L$_p$ is not hydrogen.

The carbon atom content of various hydrocarbon containing groups is indicated by a prefix designating the minimum and maximum number of carbon atoms in the moiety. For example, in defining the moiety, —COL$_5$, wherein L$_5$ is (C$_1$-C$_{12}$) alkyl means L$_5$ can be an alkyl group having from 1 to 12 carbon atoms. Additionally, any moiety so defined includes straight chain or branched chain groups. Thus, (C$_1$-C$_{12}$) alkyl as set forth above includes straight or branched chain alkyl groups having from 1 to 12 carbon atoms.

Examples of (C$_1$-C$_{12}$) alkyl are methyl, ethyl, propyl, isopropyl, isobutyl, tert-butyl, isopentyl, neopentyl, butyl, pentyl, hexyl, heptyl, octyl, nonyl, decyl, undecyl, dodecyl, and isomeric forms thereof.

Examples of ($C_3$-$C_{10}$) cycloalkyl, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

When Z is $CO_2L_5$, the novel compounds so described are used for the purposes described above in the free acid form, in ester form, or in pharmacologically acceptable salt form. When the ester form is used, the ester is any of those within the above definition of $L_5$. However, it is preferred that the ester be alkyl of 1 to 12 carbon atoms, inclusive. Of the alkyl esters, methyl and ethyl are especially preferred for optimum absorption of the compound by the body or experimental animal system, and straight-chain octyl, nonyl, decyl, undecyl, and dodecyl are especially preferred for prolonged activity.

Pharmacologically acceptable salts of the novel compounds for the purposes described above are those with pharmacologically acceptable metal cations, ammonia, amine cations, or quaternary ammonium cations. Illustrative pharmacologically acceptable cations include the following representative examples.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, and tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamine; heterocyclic amines, such as, piperidine, morpholine, pyrrolidine, piperazine, and lower alkyl derivatives thereto, such as, 1-methylpiperidine, 4-ethylmorpholine, 1-isopropylpyrrolidine, 2-methylpyrrolidine, 1,4-dimethylpiperazine, 2-methylpiperidine; and amines containing water solubilizing or hydrophilic groups, such as, mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, and procaine. Further useful amine salts are the basic amino acid salts, such as, lysine and arginine.

Examples of suitable pharmacologically acceptable quaternary ammonium cations are tetramethylammonium, tetraethylammonium, benzyltrimethylammonium, and phenyltriethylammonium.

When the compounds of this invention contain a basic nitrogen atom, the compounds are used for the purposes described in either the free base or the pharmacologically acceptable acid addition salt form.

The acid addition salts of the compounds provided by this invention are, for example, the hydrochlorides, hydrobromides, hydroiodides, sulfates, phosphates, cyclohexanesulfamates, methanesulfonates, ethanesulfonates, benzenesulfonates, or toluenesulfonates prepared by reacting the appropriate compound with the stoichiometric amount of the acid corresponding to the pharmacologically acceptable acid addition salt.

The novel $LTB_4$ analogs disclosed herein produce a multiplicity of biological responses, rendering these compounds useful for a variety of pharmacological purposes. In particular, the biological responses include bronchodilation, nasal decongestion, peripheral vascular circulatory improvement, skin disease and inflammation reduction.

Accordingly, the novel $LTB_4$ analogs of the present invention are used as agents in the study, prevention, control, and treatment of diseases and other undesirable physiological conditions in mammals, particularly humans.

The compounds of this invention affect smooth muscle contractions and cellular secretions making these compounds useful as bronchodilators or as inhibitors of cellular mediators, released from cells activated by an antigen-antibody complex, which produce undesirable physiological responses. Use of these compounds controls spasm and facilitate breathing in conditions such as bronchial asthma, bronchitis, bronchiectasis, pneumonia and emphysema.

The effect of the compounds of this invention on smooth muscle contraction were demonstrated in a standard laboratory test. Isolated prepared strips of guinea pig lung parenchyma were exposed to compounds of this invention. Certain compounds of this invention behaved as agonists because the parenchyma strips were desensitized by subsequent challenges with $LTB_4$ but were not desensitized by subsequent challenges of histamine. Other compounds of this invention behaved as antagonists of myotropic activity of $LTB_4$ at concentrations less than concentrations needed for agonist behavior.

The novel $LTB_4$ analogs herein are useful in mammals, including man, as nasal decongestants and are used for this purpose in a topical application dose range of about 10 μg to about 10 mg per ml of a pharmacologically suitable liquid vehicle or as an aerosol spray.

These compounds are also useful in treating peripheral vascular disease in humans. The term peripheral vascular disease as used herein means disease of any of the blood vessels outside of the heart and disease of the lymph vessels, for example, frostbite, ischemic cerebrovascular disease, artheriovenous fistulas, ischemic leg ulcers, phlebitis, venous insufficiency, gangrene, hepatorenal syndrome, ductus arteriosus, non-obstructive mesenteric ischemia, arteritis, lymphangitis and the like. These examples are included to be illustrative and should not be construed as limiting the term vascular disease. For these conditions the compounds of this invention are administered orally or parenterally by injection or infusion directly into a vein or artery, intravenous or intraarterial injections being preferred. The dosages of these compounds are in the range of 0.01–1.0 μg/kg of body weight administered by infusions at an hourly rate or by injection on a daily basis, the exact dose depending on the age, weight and condition of the patient and on the frequency and route of administration. Corresponding oral doses are in the range 0.05–50 mg every 2 hours, up to a maximum of 6 doses daily.

Treatment is continued for 1 to 5 days, although 3 days is ordinarily sufficient to assure long-lasting therapeutic action. In the event that systemic or side effects are observed the dosage is lowered below the threshold at which such systemic or side effects are observed.

The novel LTB$_4$ analogs of this invention are useful for treating proliferating skin diseases of man and domesticated animals, including psoriasis, atopic dermatitis, non-specific dermatitis, primary irritant contact dermatitis, allergic contact dermititis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domestic animals. These compounds alleviate the symptoms of these proliferative skin diseases: psoriasis, for example, being alleviated when scale-free psoriasis lesion is noticeably decreased in thickness or noticeably, but incompletely cleared, or completely cleared.

For these purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients; constitute from about 0.1% to about 15% by weight of the composition, preferably from about 0.5% to about 2% by weight of composition. In addition to topical administration, injection may be used, as intradermally, intra- or peri-lesionally, or subcutaneously, using appropriate sterile saline compositions.

The LTB$_4$ analogs of this invention are useful as anti-inflammatory agents for inhibiting chronic inflammation in mammals including the swelling and other unpleasant effects thereof using methods of treatment and dosages generally used for similar therapeutic agents known in the art.

The effect of the compounds of this invention to inhibit LTB$_4$ binding to human neutrophil membranes were demonstrated in a standard laboratory test. The ability of compounds of this invention at varying concentrations to competitively bind to the LTB$_4$ receptor in human neutrophil membranes in the presence of a known concentration of LTB$_4$ were measured. The tests also demonstrated the compounds effected neutrophil aggregation.

Hammerstrom, et al., Science Vol. 197, 994–996 (1977) notes the role of the leukotrienes including LTB$_4$ in psoriasis. Doig, et al., Prostaglandins, Vol. 20, 1007–1019 (1980) and Lin, et al., J. Clin. Invest., Vol 70, 1058 (1982) discloses the leukotrienes including LTB$_4$ block platelet thrombus formation. Dawson, et al., SRS-A and Leukotrienes, 219–226, Wiley and Sons (1981) notes the leukotrienes including LTB$_4$ inhibitors block neutrophil "recruitment" during inflammatory diseases such as arthritis.

The leukotrienes including LTB$_4$, have been implicated in essential hypertension, Chand, et al., Microcirculation, 111–123 (1981), and gout, Rae, et al., Lancet, 1122–1124 (Nov. 20, 1982), indicating that the compounds disclosed and claimed herein are useful in treating these conditions as well. Further, neutrophil depletion, such as that induced leukotrienes including LTB$_4$, cause a significant decrease in infarct size following circumflex artery occlusion, Romson, et al., Circulation, 85 (1982). Thus, these compounds may be useful in the protection of the myocardium following infarct.

The compounds of the present invention are also useful for the prevention or treatment of deep vein thrombosis (DVT). DVT is the thrombosis (clot formation) of the lower limb deep veins (deeply situated veins). Such thrombosis is frequently a result of major surgery, massive trauma, myocardial infarction, neoplasia, or pregnancy. The term "deep vein thrombosis" or "DVT" encompasses the thrombosis resulting from these or any other causes. The term "prevention" means the total or partial avoidance of clot formation in the deep veins of a mammal.

Any convenient route of administration is employed. Oral formulation and oral administration are preferred route for use in humans although parenteral; intravenous, intraperitoneal, and intramuscular, administration can also be used.

The dosage regimen for the compounds used to treat deep vein thrombosis will depend on a variety of factors, including the type, age, weight, sex, and medical condition of the mammal, and most importantly on the risks and probable consequences of deep vein thrombosis. It is within the skill of the attending physician or veterinarian to determine the risks of deep vein thrombosis, and to prescribe an effective amount of the leukotriene antagonist claimed herein. The dosage is in the range of about 0.01 to about 1 mg/kg/minute by intravenous infusion, or about 0.1 to about 50 mg/kg/day by oral administration. Equivalent dosages for other routes of administration are also employed.

The compounds of this invention are administered in a variety of dosage forms: orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. When treating conditions for which a dosage range is not specified above, doses in the range of about 0.01 to 50 mg per kg of body weight are used 1 to 4 times a day. The exact dose is determined by the age, weight, and condition of the patient or animal and on the frequency and route of administration.

The compounds of this invention are effectively administered to human asthma patients by any convenient route such as oral inhalation, aerosol inhalation, parenterally, transdermally or topically.

For administration by the oral inhalation route with conventional nebulizers or by oxygen aerosolization it is convenient to provide the active ingredient in dilute solution, preferably at concentrations of about 1 part by weight of medicament to about 100 to 200 parts by weight of total solution. Conventional additives such as, sodium chloride, sodium citrate, citric acid and sodium bisulfite, may be employed to stabilize these solutions or to provide isotonic media.

For administration of the active ingredient in aerosol form for inhalation therapy the composition as a self-propelled dosage unit can comprise the active ingredient; an inert propellant (such as a mixture of dichlorodifluoromethane and dichlorotetrafluoroethane); a co-solvent (such as ethanol); flavoring materials and stabilizers. Instead of a co-solvent, a dispensing agent such as oleyl alcohol could be used. A suitable means to employ the aerosol inhalation therapy technique is described in U.S. Pat. No. 2,868,691.

For the treatment of asthma these compounds can be combined advantageously with other anti-asthmatic agents, such as sympathomimetics (isoproterenol, phenylephedrine, ephedrine, etc.); xanthine derivatives (theophylline and aminophylline); and/or corticosteroids (ACTH and prednisolone).

The compounds of this invention are formulated into compositions for administration to humans and animals in unit dosage forms containing suitable quantities of the compound. Suitable administrations means include: tablets; capsules; pills; powders; granules; sterile parenteral solutions or suspensions; eye drops; oral solutions or suspensions, and oil in water and water in oil emulsions.

For oral administration solid or fluid unit dosage forms can be prepared. For preparing solid compositions, the compounds of this invention are mixed with conventional ingredients such as talc, magnesium stearate, dicalcium phosphate, magnesium aluminum silicate, calcium sulfate, starch, lactose, acacia, methylcellulose, and/or functionally similar pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

For preparing fluid compositions, the compounds of this invention are dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent. Suspensions are prepared in an aqueous vehicle with the aid of a suspending agent such as acacia, tragacanth, or methylcellulose.

For parenteral administration, fluid unit dosage forms are prepared utilizing the compound and a sterile vehicle, preferably water. The compounds of this invention, depending on the vehicle and concentration used, can be either suspended or dissolved in the vehicle. In preparing solutions, the compound is dissolved in a suitable vehicle, filtered, sterilized, loaded into a suitable vial or ampoule and sealed. Adjuvants such as a local anesthetic, preservative and buffering agents, can be dissolved in the vehicle. To enhance the stability, the composition can be frozen after loading into the vial and the vehicle removed. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. These compounds can be sterilized by exposure to ethylene oxide or an equivalent sterilizing gas before suspending in the sterile vehicle. A surfactant or wetting agent is included in the composition to facilitate uniform distribution of the compound.

For inhalation, powders, solutions, or aerosols can be prepared. Powders are prepared by mixing a suitable pharmaceutically useful compound of this invention with a solid base compatible with lung tissue, preferably lactose. The powders are packaged in a device adapted to emit a measured amount of powder when inhaled through the mouth.

Aqueous solutions are prepared by dissolving the appropriate compound of this invention in water, adding salt to provide an isotonic solution and buffering to a pH compatible with inhalation. The solutions are dispersed in a spray device or nebulizer and sprayed into the mouth while inhaling.

Aerosols are prepared by dissolving the appropriate compound of this invention in water or ethanol, mixing with a volatile propellant and placing the composition in a pressurized container having a metering valve to release a predetermined amount of material.

The volatile propellant employed is one which has a boiling point below 65° F. at atmospheric pressure. For use in compositions intended to produce aerosols for medicinal use, the propellant should be non-toxic. Among the suitable propellants which may be employed are the lower alkanes containing up to 5 carbon atoms, such as butane and pentane, or a lower alkyl chloride, such as methyl, ethyl or propyl chlorides. Other suitable propellants are fluorinated and fluorochlorinated lower alkanes or mixtures thereof, such as, dichlorodifluoromethane, dichlorotetrafluoroethane, trichloromonofluoromethane, dichloromonofluoromethane, monochlorodifluoromethane, trichlorotrifluoroethane, difluoroethane and monochlorotrifluoromethane.

The $LTB_4$ analogs of this invention represented by formulas I and II are prepared by various procedures which are all generally known in the art. The preparation of the compounds this invention are outlined in the charts described below.

Chart A outlines the preparation of some of the compounds of formula I, where Y is A-1 to A-4, and the compounds of formula II, where P is A-5 to A-8. The meta-substituted aromatic compound, A-I where A-I is $AF_1$ to $AF_4$, is monolithiated by n-butyllithium and the anion is reacted with dimethylformamide in diethyl ether to give the haloaldehyde, A-II. The haloaldehyde reacts with a Wittig reagent, AW, formed by reacting a known carboxyphosphonium halide with known bases such as lithium (bis)trimethylsilylamide in THF, to give a mixture of cis and trans olefin acids, A-III. Wittig reagents defined by AW are commercially available or are prepared by known methods. Specific examples of Wittig reagents within the scope of this invention are disclosed in U.S. Pat. No. 3,776,941.

To prepare the compounds of this invention where $M_1$ and A taken together are a lactone, the mixture of olefin acids is lactonized with potassium iodide in the presence of potassium bicarbonate in THF/water to give the iodolactone, A-IV where E is Iodo. Alternatively, the mixture of olefin acids is lactonized with N-phenylselenylphthalimide in the presence of camphorsulfonic acid in methylene chloride to give the selenolactone, A-IV where E is $Se(C_6H_5)$. The selenolactone and the iodolactone are reduced with tri-n-butyltin hydride in the presence of azo-(bis)isobutylnitrile in toluene to give the lactone, A-V.

To prepare compounds of this invention where $M_1$ and A taken together are a lactol, the lactone, A-V is reduced with sodium (bis)2-methoxyethoxy aluminum hydride in toluene at $-20°$ to $0°$.

To prepare compounds of this invention where $M_1$ is hydroxy or a protected hydroxy and hydrogen, the lactone, A-V, is hydrolyzed to the hydroxy acid with aqueous sodium hydroxide in methanol to give the hydroxy acid, A-VI. The hydroxy group can be protected by procedures already described.

To prepare compounds of this invention where $M_1$ is hydroxy or a protected hydroxy and methyl, the hydroxy acid, A-VI is oxidized to the ketone by known methods and then reacted with a methyl lithium or a methyl grignard reagent to give the desired methylated compound, A-VII.

To prepare compounds of this invention where $R_5$ is the epoxide, the iodolactone, A-IV where E is Iodo, reacts in the presence of potassium carbonate in methanol gives the epoxy ester, A-VIII. The epoxy ester, A-VIII, reacts with sodium cyanoborohydride in boron trifluoride etherate to open the epoxide giving compounds where $M_1$ is hydroxy and hydrogen.

The preparation of compounds of this invention is completed by adding the $B-C\cong C-CH_2C(M_2)-C\cong C-$ side chain using a palladium-copper catalyzed cross coupling reaction, described by, K. Sonogashira, et al., Tetrahedron Letters, 4467 (1975) and S. Takahashi, et al., Synthesis, 627 (1980). Compounds A-III, A-V, A-VI, A-VII or A-VIII and $B-C\cong C-CH_2C(M_2)-C\equiv CH$ react in the presence of (bis)-triphenylphosphine palladium dichloride and cuprous iodide in triethylamine at 50° to 70° for 3 to 6 hours to give the coupled compounds where $B-C\cong C-CH_2C(M_2)-C\equiv C-$ has replaced X—. The coupling reaction using A-III gives A-IX, A-V gives A-X, A-VIII gives A-XI.

To prepare compounds of this invention where Z is $-CH_2OH$, $M_1$ is hydroxy, A-X is reduced with an excess of sodium (bis)2-methoxyethoxy aluminum hydride in toluene at $-20°$ to $0°$. These reaction conditions also reduce any propargylic triple bonds to trans double bonds. A similar reduction of compounds A-IX and A-XI reduces the acid to the primary alcohol. The primary alcohol of the reduced compounds is selectively oxidized to the free carboxylic acid by reacting the compounds with elemental oxygen in the presence of platinum black in water/acetone.

Alternatively, the preparation of the compounds of this invention can be completed by a sequential process to replace X- with $B-C\cong C-CH_2C(M_2)-C\equiv C-$. Compound A-II is ketalized by known procedures and is reacted with commercially available monotrimethylsilyl acetylene in the presence of (bis)triphenylphosphine palladium dichloride and cuprous iodide in diethylamine at 45° for 6 hours to give the trimethylsilyl alkyne, A-XII. Hydrolysis of the trimethylsilyl alkyne with potassium hydroxide in methanol/water or tetrabutyl-ammonium fluoride in THF at room temperature gives the alkyne which is deprotonated by LDA in THF at $-78°$ and added $B-C\cong C-CH_2CHO$ at $-78°$ to give A-XIII. The procedures described for A-II are used following hydrolysis of the ketal to the aldehyde to give compounds of this invention where $M_2$ is hydroxy and hydrogen. Compound A-II can also be coupled to $B-C\cong C-CH_2C(M_2)-C\equiv CH$ by procedures already described.

To prepare compounds of this invention where $M_2$ is hydroxy or a protected hydroxy and methyl, A-XIII is oxidized to the ketone by known methods and then reacted with a methyl lithium or a methyl grignard reagent to give the desired methylated compounds.

To prepare compounds of this invention with cis double bonds, triple bonds are partially hydrogenated with known catalysts to give the cis stereochemistry. To prepare compounds of this invention with trans double bonds, propargylic triple bonds are reduced with sodium (bis)methoxyethoxy aluminum hydride in toluene at $-20°$ to $0°$ to give the trans stereochemistry. Other cis or trans double bonds are prepared by known methods.

When Z is $CO_2CH_3$, the methyl ester is saponified in aqueous lithium or sodium hydroxide to give the acid. When Z is $CO_2CH_3$ or $CO_2H$, the acid or methyl ester is reduced to the primary alcohol by reacting the compounds with an excess of lithium aluminum hydride in THF at room temperature.

To prepare compounds of this invention where $R_5$ is $-CH(R_6)-C(M_1)-$, epoxide A-VIII is opened with a known thiol compound in the presence of base. The sulfide resulting from the epoxide opening can be oxidized to the sulfoxide or the sulfone by known methods.

When Z is $CO_2H$ and an alkyl or cycloalkyl ester is desired, esterification is accomplished by reacting the acid with an appropriate diazohydrocarbon. For example, diazomethane, diazoethane, diazobutane, 1-diazo-2-ethylhexane, and diazodecane give the methyl, ethyl, butyl, and 2-ethylhexyl and decyl esters. Similarly, diazocyclohexane gives the cyclohexyl ester. Esterification with diazohydrocarbons is carried out by mixing the acid with the diazohydrocarbon in a suitable inert solvent, preferably diethyl ether. After the esterification reaction is complete the solvent is removed by evaporation, and the ester is purified by conventional methods, preferably by chromatography. It is preferred that contact of the acid with the diazohydrocarbon be no longer than necessary to effect the desired esterification, preferably about 1 to 10 minutes, to avoid undesired side reactions. Diazohydrocarbons are known in the art or can be prepared by methods known in the art. See, for example, Organic Reactions, John Wiley and Sons, Inc., New York, N.Y., Vol. 8, pp. 389-394 (1954).

An alternative method for preparing alkyl or cycloalkyl esters comprises transforming the acid to the corresponding substituted ammonium salt and reacting that salt with an alkyl iodide. Suitable alkyl iodides are methyl iodide, ethyl iodide, butyl iodide, isobutyl iodide, tert-butyl iodide, cyclopropyl iodide, or cyclopentyl iodide.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples include: ethanol, acetone, ethyl acetate, diethyl ether and benzene. At least a stoichiometric amount of the amine corresponding to the desired cation is then added to that solution. If the resulting salt does not precipitate, it is usually obtained in solid form by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The hydroxyl groups of the compounds of the present invention may be protected by various groups generally employed in the art if protection of the hydroxyl functions is desirable or necessary during the preparation of the compounds. Although any of the various protecting groups known in the art may be employed, those preferred are tetrahydropyranyl (THP) and tert-butyldimethylsilyl. Particularly, THP is a preferred protecting group during the various reactions required to add the side chains and t-butyldimethylsilyl is a preferred group to employ during separation of the isomers. Of course it may be useful or desirable to utilize protecting groups which may be selectively hydrolyzed.

As indicated hereinabove, $L_p$ is hydrogen or a protecting group. Those protective groups within the scope of $L_p$ are any group which replaces an hydroxyl hydrogen, is not reactive to the reagents used in subsequent transformations and is readily removed to regenerate the original hydroxyl group hydrogen. Many protective groups are known in the art. For reference see, E. J. Corey, Proceedings of the Robert A. Welch Foundation Conferences on Chemical Research, *Organic Synthesis XII*, 51-79 (1969).

When the protecting group, $L_p$, is a tetrahydropyranyl or a tetrahydropyranyl ether derivative the protected hydroxy compounds are prepared by reacting of the hydroxyl containing compound with 2,3-dihydropyran in an inert solvent in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°-50° C.

When the protecting group, $L_p$, is silyl reagent, selective protection is possible. Some silylating reagents are non-selective all hydroxyls of a molecule are silylated. Other silylating reagents are selective because one or more hydroxyls are silylated without affecting other hydroxyl groups. Silyl groups include trimethylsilyl, dimethylphenylsilyl, triphenylsilyl, t-butyldimethylsilyl, or methylphenylbenzylsilyl. These silyl groups are known in the art. See, for example, Pierce, *Silylation of Organic Compounds*, Pierce Chemical Company, Rockford, Ill. (1968). When silylated products are intended to be subjected to chromatographic purification, the use of silyl groups known to be unstable to chromatography (e.g., trimethylsilyl) should be avoided. When silyl groups are to be introduced selectively, silylating agents which are readily available and known to be useful in selective silylations are used. For example, t-butyldimethylsilyl groups are used when selective introduction is required. When silyl groups are to be selectively hydrolyzed in the presence of other protective groups the use of silyl groups which are readily available and known to be easily hydrolyzed with tetra-n-butylammonium fluoride are used. A particularly useful silyl group for this purpose is t-butyldimethylsilyl.

The protective groups as defined by $L_p$ are generally removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

$L_p$ may also be an acyl protective group. Methods known in the art are used to prepare acyl derivatives of hydroxy compounds. For example, benzoic acid reacts with the hydroxy compound in the presence of a dehydrating agent, such as p-toluenesulfonyl chloride or dicyclohexylcarbodiimide to give the acyl derivative. Alternatively, an acid anhydride such as benzoic anhydride, is used instead of the free acid. The preferred method to prepare acyl derivatives uses the appropriate acyl halide. For example, benzoyl chloride reacts with the hydroxy compound in the presence of a hydrogen chloride scavenger, such as, pyridine or triethylamine. The reaction is carried out under a variety of conditions, using procedures known in the art. The reaction occurs at mild temperatures 0°-60° C. by contacting the reactants in excess pyridine or an inert solvent such as benzene, toluene, or chloroform. The acylating agent is used either in stoichiometric amount or in substantial stoichiometric amount or in substantial stoichiometric excess.

The acyl protective groups are removed by deacylation. Alkali metal carbonate or hydroxide are employed effectively at ambient temperatures for this purpose. For example, potassium carbonate or hydroxide in aqueous methanol at about 25° C. is used.

Purification, isolation and separation of isomeric and diastereomeric mixtures is achieved by well known means, including column chromatography.

The following examples also describe the compounds of this invention.

EXAMPLE 1

1,1-Dimethoxy-3-nonyne

1-Heptyne (50 ml, 381 mmole) is dissolved in 360 ml dry THF in a flame dried 2000 ml 3-neck round bottom flask under nitrogen. The solution is cooled to 0° C. and treated with n-butyllithium (232 ml, 360 mmole) dropwise over 40 minutes via a dropping funnel. The reaction mixture is stirred 30 minutes at 0° C., treated with hexamethylphosphoric triamide (68 ml, 391 mmole), and stirred an additional 30 minutes at 0° C. 1,1-Dimethoxy-2-bromoethane (43 ml, 364 mmole) is added dropwise to the reaction mixture over 10 minutes at 0° C. The reaction mixture is stirred 3 hours at 0° C. and an additional 72 hours at room temperature. The mixture is subsequently quenched with 5 ml water and the THF removed in vacuo. The amber oily residue is dissolved in 200 ml diethyl ether and poured into 100 ml 50% saturated sodium chloride. The aqueous layer is extracted with 3×75 ml diethyl ether. The organics are combined, washed with 6×50 ml 50% saturated sodium chloride, and dried over anhydrous magnesium sulfate. The diethyl ether is removed in vacuo and the red oily residue distilled under reduced pressure. After a 5 ml forerun, the fraction boiling at 65°-67° C. (0.5 mm) is collected to provide 42 g of the title compound as a colorless oil. Following the above procedure gives the title compound having the physical characteristic described below:

TLC (silica gel 60, F-254): $R_f = 0.16$ (5% ethyl acetate/hexane).

EXAMPLE 2

1,1-Dimethoxy-3-Z-nonene 1,1-Dimethoxy-3-nonyne (8.35 g, 45.3 mmole) is dissolved in 130 ml hexane in a 250 ml one-neck round bottom flask. The solution is treated successively with quinoline (6 drops) and 5% palladium on calcium carbonate (360 mg) in a single lot. The reaction mixture is hydrogenated at atmospheric pressure until the theoretical amount of hydrogen (1015 ml) is taken up. The reaction mixture is immediately filtered through celite and the filter cake washed well with fresh hexane. The filtrate is washed with 2×45 ml saturated cupric sulfate, dried over magnesium sulfate, and concentrated in vacuo to afford 8.3 g of the title compound as a colorless oil. Following the above procedure gives the title compound having the physical characteristic described below:

TLC (silica gel 60, F-254): $R_f=0.36$ (10% ethyl acetate/hexane).

EXAMPLE 3

3-Z-nonenal 1,1-Dimethoxy-3-Z-nonene (1.404 g, 7.54 mmole) is dissolved in 25 ml pentane in a 100 ml one-neck round bottom flask. The solution is treated with formic acid (6.7 ml) and stirred vigorously for 65 minutes at room temperature. The mixture is diluted with 40 ml saturated sodium chloride and the layers separated. The aqueous layer is extracted with 5×20 ml hexane. The organics are combined, washed carefully with 1×50 ml saturated sodium bicarbonate, and dried over anhydrous magnesium sulfate. The dried organics are concentrated in vacuo to afford 1.01 g of the title compound as a pungent pale oil. Following the above procedure gives the title compound having the physical characteristic described below:

$^1$H-NMR (CDCl$_3$, TMS): 0.73–1.09; 1.13–1.65; 1.88–2.26; 3.11–3.30; 5.41–5.91; 8.70.

EXAMPLE 4

3-Hydroxy-1-trimethylsilyl-undec-5Z-ene-1-yne

Trimethylsilylacetylene (6.9 g, 48.6 mmole) is dissolved in 125 ml dry THF in a flamed dried 500 ml 3-neck round bottom flask under nitrogen at −78° C. The solution is treated with n-butyllithium (29.9 ml, 46.3 mmole) slowly dropwise over 10 minutes and stirred 30 minutes at −78° C. The reaction mixture is subsequently treated slowly dropwise with boron trifluoride etherate (6.0 ml, 48.8 mmole) and the resultant mixture is stirred 20 minutes at −78° C. 3-Z-Nonenal (6.2 g, 44 mmole), in 3×12 ml dry THF, is added rapidly dropwise to the reaction mixture at −78° C. The reaction is warmed to 0° C. and stirred an additional 20 minutes. The mixture is quenched with 100 ml saturated sodium chloride, the layers separated, and the aqueous phase extracted with 3×60 ml diethyl ether. The organics are combined, dried over magnesium sulfate, and concentrated in vacuo to a dark yellow oil (10.5 g). The crude oil is chromatographed over 200 g silica gel (230–400 mesh), eluting with 6% ethyl acetate/hexane and collecting 60 ml fractions. Fractions 8–16 are combined and concentrated to afford 6.3 g of the title compound as a pale yellow oil. Following the above procedure gives the title compound having the physical characteristic described below:

TLC (silica gel 60, F-254): $R_f=0.36$ (10% ethyl acetate/hexane).

EXAMPLE 5

3-Hydroxy-undec-5Z-ene-1-yne Method A

3-Hydroxy-1-trimethylsilyl-undec-5Z-ene-1-yne (6.3 g, 26 mmole) is dissolved in 100 ml dry THF in a flame dried 250 ml one-neck round bottom flask under nitrogen. The solution is cooled to 0° C. and treated slowly dropwise with tetrabutylammonium fluoride (1.0M/THF; 32 ml, 32 mmole). The reaction is stirred one hour at 0° C., quenched with 50 ml 90% saturated sodium chloride, and the THF removed in vacuo. The aqueous residue is extracted with 4×20 ml diethyl ether. The organics are combined, washed with 1×50 ml saturated sodium chloride, and dried over magnesium sulfate. The organics are concentrated in vacuo to a dark amber oil. The crude oil is chromatographed over 100 g silica gel (230–400 mesh), eluting with 8% ethyl acetate/hexane and collecting 20 ml fractions. Fractions 16–39 are combined and concentrated to provide 3.87 g of the title compound as a yellow oil.

EXAMPLE 6

3-Hydroxy-undec-5Z-ene,-1-yne Method B

A 0.6M acetylene/THF solution is prepared by bubbling acetylene gas into 160 ml dry THF (to saturation) in a flame dried 500 ml 3-neck round bottom flask under nitrogen at room temperature. The solution is cooled to −78° C. An oven dried 250 ml 3-neck round bottom flask under nitrogen is charged with 14 ml dry THF and diisopropylamine 7.5 ml (53.9 mmole). The solution is cooled to −25° C. and treated with n-butyllithium (32.7 ml, 50.7 mmole/hexane) slowly dropwise over 35 minutes via syringe drive. The mixture is stirred 30 minutes at −25° C. The lithium diisopropylamide is added slowly dropwise to the acetylene solution at −78° C. over 60 minutes. The reaction mixture is stirred 20 minutes at −78° C. 3-Z-Nonen-al (4.4 g, 31.6 mmole), in 1×10 ml dry THF (5 ml rinse), is added rapidly dropwise to the reaction mixture over 10 minutes via syringe drive. The reaction mixture is stirred 45 minutes at −78° C. and quenched at −78° C. with 10 ml saturated ammonium chloride. The mixture is warmed to room temperature and the organic solvents removed in vacuo. The aqueous residue is diluted with 50 ml 90% saturated ammonium chloride and extracted with 5×30 ml diethyl ether. The organics are combined, dried over magnesium sulfate and concentrated in vacuo to a yellow oil (4.75 g).

The oil is chromatographed over 240 g silica gel (230–400 mesh), eluting with 4% ethyl acetate/hexane, and following a 2000 ml forerun collecting 50 ml fractions. Fractions 10–33 are combined and concentrated to afford 3.04 g of the ethynyl alcohol 7 as a pale yellow oil. Following the above procedures gives the title compound having the physical characteristic described below:

TLC (silica gel 60, F-254): $R_f=0.47$ (30% ethyl acetate/hexane).

EXAMPLE 7

2-(3-[2-Trimethylsilylethynyl]phenyl)-1,3-dioxolane

Trimethylsilyl acetylene (5.2 ml, 36.8 mmole), 2-(3-bromophenyl)-1,3-dioxolane (5.0 ml, 33.0 mmole), and bis(triphenylphosphino)palladium dichloride (500 mg, 0.71 mmol) are combined in 95 ml diethylamine in a flame dried 250 ml 3-neck round bottom flask under argon. The reactants are stirred 10 minutes at room temperature, and cuprous iodide (67 mg, 0.32 mmole) is added in a single lot. The reaction mixture is heated at 45° C. for 6 hours. The mixture is allowed to cool to room temperature. The diethylamine is removed in vacuo and the black residue partitioned between 50 ml 50% saturated sodium chloride and 50 ml ethyl acetate. The layers are separated and the aqueous phase extracted with 3×25 ml ethyl acetate. The organics are combined, dried over magnesium sulfate, and concentrated in vacuo to a black oil (9.12 g).

The oil is chromatographed over 320 g silica gel (230-400 mesh), eluting with 5% ethyl acetate/hexane and collecting 60 ml fractions. Fractions 23-41 are combined and concentrated to afford 7.4 g of a pale oil, a mixture of the title compound and starting material. Following the above procedure gives the title compound having the physical characteristic described below:

TLC (silica gel 60, F-254): $R_f$=0.27 (10% ethyl acetate/hexane).

EXAMPLE 8

2-(3-Ethynylphenyl)-1,3-dioxolane 2-(3-[2-Trimethylsilylethynyl]phenyl)-1,3-dioxolane contaminated with 40% 2-(3-bromophenyl)-1,3-dioxolane (3.85 g, 9.4 mmole), is dissolved in 60 ml methanol in a 100 ml 3-neck round bottom flask. The solution is treated with 1N potassium hydroxide (18 ml, 18 mmole) in one lot at room temperature. The reaction mixture is stirred one hour at room temperature and the methanol removed in vacuo. The aqueous residue is extracted with 4×25 ml ethyl acetate. The organics are combined, washed with 1×25 ml saturated sodium chloride, and dried over magnesium sulfate. The dried organics are concentrated in vacuo to a crude yellow oil (3.2 g).

The oil is chromatographed over 100 g silica gel (230-400 mesh), eluting with 10% ethyl acetate/hexane and collecting 20 ml fractions. Fractions 16-21 are combined and concentrated to afford 1.32 g of the contaminating bromo-acetal. Fractions 22-30 are combined and concentrated to provide 1.32 g of the title compound as a pale oil. Following the above procedure gives the title compound having the physical characteristic described below:

TLC (silica gel 60, F-254): $R_f$=0.19 (10% ethyl acetate/hexane).

EXAMPLE 9

2-(3-[3-Hydroxy-undec-5Z-ene-1-ynl]phenyl)-1,3-dioxolane Method A

3-Hydroxy-undec-5Z-ene-1-yne (143 mg, 0.86 mmole) and 2-(3-bromophenyl)-1,3-dioxolane (1 30 μl, 0.86 mmole) are combined in 2 ml diethylamine in a flame dried 25 ml 2-neck round bottom flask under nitrogen. The solution is treated with bis(triphenylphosphino)palladium dichloride (12 mg, 17 μmole) and stirred 20 minutes at room temperature. The mixture is subsequently treated with cuprous iodide (2 mg, 8 mmole) and immediately heated to 45° C. The reaction mixture is heated at 45° C. for 4 hours and the volatiles removed in vacuo. The residue is partitioned between 10 ml 50% saturated sodium chloride and 10 ml ethyl acetate. The layers are separated and the aqueous phase extracted with 3×10 ml ethyl acetate. The organics are combined, dried over magnesium sulfate, and concentrated in vacuo to a dark oil (314 mg).

The oil is chromatographed over 8 g silica gel (230-400 mesh), eluting with 15% ethyl acetate/hexane and collecting 3 ml fractions. Fractions 22-45 are combined and concentrated to provide 130 mg of the title compound as a yellow oil. Following the above procedure gives the title compound having the physical characteristic described below:

TLC (silica gel 60, F-254): $R_f$=0.28 (30% ethyl acetate/hexane).

EXAMPLE 10

2-(3-[3-Hydroxy-undec-5Z-ene-1-ynyl]phenyl)-1,3-dioxolane Method B

Diisopropylamine (1.05 ml, 7.52 mmole) is dissolved in 35 ml dry THF in an oven dried 100 ml 3-neck round bottom flask under nitrogen. The solution is cooled to −78° C., treated dropwise with n-butyllithium (4.22 ml, 6.54 mmole), and stirred for 30 minutes. 2-(3-Ethynylphenyl)-1,2-dioxolane (1.20 g, 6.89 mmole), in 3×3 ml dry THF, is added slowly dropwise to the reaction mixture at −78° C. The mixture is stirred 15 minutes at −78° C. and treated slowly dropwise with 3Z-nonen-al (1.01 g, 7.2 mmole) in 3×3 ml dry THF. The reaction is stirred one hour at −78° C., warmed to 0° C. for 15 minutes, and quenched with 35 ml 90% saturated sodium chloride. The mixture is extracted with 4×25 ml ethyl acetate. The organics are combined, washed with 1×50 ml saturated sodium chloride, and dried over magnesium sulfate. The organics are concentrated in vacuo to a crude yellow oil (2.6 g).

The oil is chromatographed over 60 g silica gel (230-400 mesh), eluting with 15% ethyl acetate/hexane and collecting 20 ml fractions. Fractions 36-70 are combined and concentrated to afford 1.42 g of the title compound as a pale oil. Following the above procedures gives the title compound having the physical characteristic described below:

$^1$H-NMR (CDCl$_3$, TMS): 0.75-1.00; 1.15-1.50; 1.96-2.30; 2.46-2.80; 3.94-4.17; 4.48-4.73; 5.33-5.90; 5.80; 7.22-7.69.

EXAMPLE 11

2-(3-[3-Hydroxy-undec-5Z-1E-dien-1-yl]phenyl)-1,3-dioxolane

Sodium bis(2-methoxyethoxy) aluminum hydride (3.4M/toluene; 6.5 ml, 20.9 mmole) is dissolved in 25 ml dry toluene in an oven dried 100 ml 3-neck round bottom flask under nitrogen at 0° C. The solution is cooled to −78° C. 2-(3-[3-Hydroxy-undec-5Z-ene-1-ynyl]phenyl)-1,3-dioxolane (2.6 g, 8.3 mmole), in 3×5 ml dry toluene, is added slowly dropwise to the reaction mixture at −78° C. The reaction is stirred 25 minutes at 78° C. warmed to 0° C., and stirred an additional one hour. The reaction mixture is quenched with 5 ml water, diluted with 25 ml ethyl acetate, and stirred vigorously with 25 ml 0.5M sodium potassium tartrate for one hour. The layers are separated and after dilution with 40 ml saturated sodium chloride the aqueous layer is extracted with 4×25 ml ethyl acetate. The organics are combined, washed with 1×50 ml saturated sodium chloride, and dried over magnesium sulfate. The organics are concentrated in vacuo to a pale oil (2.71 g).

The crude oil is flash filtered over 50 g silica gel (230-400 mesh), eluting with 30% ethyl acetate/hexane and collecting 8 ml fractions. Fractions 19-45 are combined and concentrated to afford 2.51 g of the title compound as a pale oil. Following the above procedure gives the title compound having the physical characteristic described below:

TLC (silica gel 60, F-254): R$_f$=0.26 (30% ethyl acetate/hexane).

EXAMPLE 12

3-(3-Hydroxy-undec-5Z-1E-dien-1-yl)-benzaldehyde 2-(3-[3-Hydroxy-undec-5Z-1E-dien-1-yl]phenyl)-1,3-dioxolane (359 mg, 1.13 mmole) is dissolved in 2 ml 80% (v/v) acetic acid/water in a 50 ml one-neck round bottom flask under nitrogen. The reaction mixture is stirred one hour at room temperature, neutralized with saturated sodium bicarbonate, and extracted with 4×15 ml diethyl ether. The organics are combined, washed successively with 1×25 ml saturated sodium bicarbonate and 1×25 ml saturated sodium chloride, and dried over magnesium sulfate. The organics are concentrated in vacuo to afford 305 mg of aldehyde 21 as a pale oil. Following the above procedure gives the title compound having the physical characteristic described below:

TLC (silica gel 60, F-254): −Rf=0.32 (30% ethyl acetate/hexane).

EXAMPLE 13

5-Hexenoic acid, 6-[3-(3-ydroxy-1,5-undecadienyl)-phenyl]-(E,E,Z)-

4-Carboxybutyl-triphenylphosphonium bromide (1.09 g, 2.46 mmole) is suspended in 4 ml dry THF in a flame dried 50 ml 2-neck round bottom flask under nitrogen. The suspension is treated dropwise with lithium bis(trimethylsilyl)amide (4.7 ml, 4.7 mmole) at room temperature and stirred for 20 minutes at that temperature. 3-(3-Hydroxy-undec-5Z-1E-dien-1-yl)-benzaldehyde (305 mg, 1.12 mmole), in 3×1 ml dry THF, is added slowly dropwise to the red ylid at room temperature. The reaction mixture is stirred 3 hours at room temperature, quenched with 25 ml water, and the organic solvent removed in vacuo. The pH of the aqueous residue is adjusted to 3 with 5% hydrochloric acid (pH meter) and the mixture extracted with 4×25 ml dichloro-methane. The organics are combined, washed with 1×25 ml saturated sodium chloride, and dried over magnesium sulfate. The organics are concentrated in vacuo to a crude pale oil (748 mg).

The oil is adsorbed onto 1.2 g silica gel (230–400 mesh) and this material is chromatographed over 15 g silica gel (230–400 mesh), eluting with 25% acetone/hexane and collecting 3 ml fractions. Fractions 22–54 are combined and concentrated to afford 297 mg of the compounds as an 80:20 trans/cis mixture. Following the above procedure gives the title compound having the physical characteristic described below:

TLC (silica gel 60, F-254): R$_f$=0.27 (50% acetone/hexane).

EXAMPLE 14

6-(3-[3-Hydroxy-undec-1E,5Z-dien-1-yl]phenyl)-5-hexenoic acid methyl ester

Ethereal diazomethane is prepared by adding N-nitroso-N-methylguanidine to 15 ml of diethyl ether layered over 20 ml 45% aqueous potassium hydroxide in a 50 ml erlenmyer flask at 0° C., until a persistent yellow color is obtained. The yellow ether layer is carefully decanted into a second erlenmyer flask containing 10 ml diethyl ether over a single layer of solid potassium hydroxide pellets, also at 0° C. The ethereal diazomethane thus prepared is added via pipette to a solution of 6-(3-[3-hydroxy-undec-1E,5Z-dien-1-yl]phenyl)-5E-hexenoic acid and 6-(3-[3-hydroxy-undec-1E,5Z-dien-1-yl]phenyl)-5Z-hexenoic acid (29 mg, 0.081 mmole) in 1 ml diethyl ether at 0° C. until a gross excess of reagent has been added as signified by a persistent yellow color in the reaction mixture. The reaction mixture is concentrated in vacuo to a crude yellow oil (30.1 mg).

The oil is flash filtered over 750 mg silica gel (230–400 mesh), eluting with 15% ethyl acetate/hexane and collecting 0.5 ml fractions. Fractions 6–13 are combined and concentrated to afford 12 mg of the title compounds as a pale oil. Following the above procedure gives the title compound having the physical characteristic described below:

TLC (silica gel 60, F-254): R$_f$=0.67 (50% acetone/hexane).

EXAMPLE 15

6-(3-Bromophenyl)-5-hexenoic acid

4-Carboxybutyltriphenylphosphonium bromide (29.3 g, 66 mmole) is suspended in 125 ml dry THF in a flame dried 500 ml 3-neck round bottom flask under nitrogen. The suspension is treated slowly dropwise with lithium bis(trimethylsilyl)amide (125 ml, 125 mmole) via a dropping funnel at room temperature. The mixture is stirred one hour as the red ylid formed. m-Bromobenzaldehyde (6.6 ml, 57 mmole), in 1×25 ml dry THF, is added slowly dropwise to the reaction mixture over 25 minutes (exotherm). The mixture is stirred overnight at room temperature. The reaction is quenched with 50 ml water and the excess THF removed in vacuo. The aqueous residue is diluted with 50 ml water and extracted with 2×100 ml diethyl ether. The diethyl ether layer is backwashed with 2×50 ml water. The aqueous layers are combined and the pH adjusted to 4.3 with 5% HCl (pH meter). The aqueous mixture is extracted with 3×100 ml ethyl acetate, the pH adjusted to 3.5, and the mixture further extracted with 2×50 ml ethyl acetate. The organics are combined, washed with 1×50 ml saturated sodium chloride, and dried over magnesium sulfate. The organics are concentrated in vacuo to an amber oil.

The oil is chromatographed over 400 g silica gel (230–400 mesh), eluting with 20% acetone/hexane and collecting 60 ml fractions. Fractions 23–52 are combined and concentrated to provide 14.5 g of an 85/15 trans/cis mixture of the title compounds as a yellow solid. Following the above procedure gives the title compound having the physical characteristic described below:

TLC (silica gel 60, F-254): R$_f$=0.20 (25% acetone/hexane).

EXAMPLE 16

5-(3-Bromophenyl)iodomethyl-tetrahydropyran-2-one 6-(3-Bromophenyl)-5-hexenoic acid (1.0 g, 3.72 mmole) is dissolved in 15 ml THF in a 100 ml 2-neck round bottom flask under nitrogen. The solution is diluted with 7.5 ml water, treated with solid potassium hydrogen carbonate (430 mg, 4.3 mmole), and stirred 20 minutes at room temperature. The reaction mixture is protected from light, cooled to −20° C., and treated successively portion-wise with potassium iodide (2.7 g, 16.9 mmole) and iodine (8.5 g, 33.6 mmole). The reaction is stirred 30 minutes at −20° C. and warmed to room temperature to stir overnight. The reaction mixture is diluted with saturated sodium thiosulfate until colorless. The mixture is poured into 50 ml saturated sodium bicarbonate and extracted with 4×30 ml diethyl ether. The organics are combined, dried over magnesium sulfate, and concentrated in vacuo to a crude amber oil (1.5 g). The oil is chromatographed over 40 g silica gel (230–400 mesh), eluting with 25% acetone/hexane and collecting 9 ml fractions. Fractions 16–26 are combined and concentrated to give 1.3 g of the title compound as an amber solid. Following the above procedure gives the title compound having the physical characteristic described below:

TLC (silica gel 60, F-254): $R_f$=0.23 (25% acetone/hexane).

EXAMPLE 17

5-(3-Bromophenyl)phenylselenylmethyl-tetrahydropyran-2-one 6-(3-Bromophenyl)-5-hexenoic acid (2.69 g, 10 mmole) is dissolved in 65 ml dry dichloromethane in an oven dried 250 ml 3-neck round bottom flask under argon. The solution is cooled to −20° C. and treated successively with N-phenylselenylphthalimide (3.93 g, 13 mmole) and camphorsulfonic acid (0.232 g, 1 mmole), each in single lots. The reaction mixture is warmed to room temperature and stirred overnight. The reaction mixture is washed with 1×50 ml saturated sodium bicarbonate and the precipitated phthalimide filtered off. The filtrate is dried over magnesium sulfate and concentrated in vacuo to a pasty yellow solid. The solid is dissolved in 12 ml hot acetone, allowed to cool to room temperature, and diluted with 175 ml hexane. The crystallizing mixture is refrigerated overnight. The white solid product is collected by filtration, washed with 100 ml hexane, and recrystallized 1× as described above to afford 3.88 g of the title compound as a white crystalline solid. Following the above procedure gives the title compound having the physical characteristic described below:

Melting Point: 127°–129° C. (uncorrected).

EXAMPLE 18

5-(m-Bromobenzyl)tetrahydropyran-2-one Method A 5-(3-Bromophenyl)iodomethyl-tetrahydropyran-2-one (1.03 g, 2.56 mmole) is dissolved in 15 ml dry toluene in a 100 ml one-neck round bottom flask under argon. Tributyltin hydride (0.74 ml, 2.8 mmole) is added slowly dropwise to the reaction mixture at room temperature. The reaction mixture is subsequently treated with azo-bis(isobutyrylnitrile) (42 mg, 0.256 mmole) and heated at 75° C. for 1.5 hours. The mixture is cooled to room temperature and concentrated in vacuo to a colorless oil.

The oil is chromatographed over 42 g silica gel (230–400 mesh), eluting with 10% acetone/hexane and collecting 8 ml fractions. Fractions 43–72 are combined and concentrated to provide 556 mg of the title compound as a colorless oil.

EXAMPLE 19

5(m-Bromobenzyl)tetrahydropyran-2-one Method B 5-(3-Bromophenyl)phenylselenylmethyl-tetrahydropyran-2-one (6.7 g, 15.8 mmole) is suspended in 100 ml dry toluene in an oven dried 250 ml 3-neck round bottom flask under nitrogen. The suspension is brought to solution by warming to 65° C. The solution is treated with tributyltin hydride (4.7 ml, 17.4 mmole), stirred for 10 minutes, and treated with azo(bis)isobutyrlnitrile (0.285 g, 1.74 mmole) in one lot. The reaction mixture is stirred 1.5 hours at 65° C., cooled to room temperature, and concentrated in vacuo to a pale oil. The oil is chromatographed over 250 g silica gel (230–400 mesh), eluting with 20% ethyl acetate/hexane and after a 2500 ml forerun collecting 60 ml fractions. Fractions 10–48 are combined and concentrated to afford 3.45 g of the title compound as a pale oil. Following the above procedures gives the title compound having the physical characteristic described below:

TLC (silica gel 60, F-254): $R_f$=0.24 (25% acetone/hexane); $R_f$=0.16 (30% ethyl acetate/hexane).

EXAMPLE 20

6-(3-Bromophenyl)-5,6-epoxy-hexanoic acid 5-(3-Bromophenyl)iodomethyl-tetrahydropyran-2-one (7.45 g, 18.6 mmole) is dissolved in 200 ml methanol in a 1000 ml one-neck round bottom flask under nitrogen. The reaction mixture is treated with potassium carbonate (4.7 g, 34 mmole) and stirred vigorously for one hour at room temperature. The reaction is diluted with 180 ml 90% saturated sodium chloride and the bulk of the methanol removed in vacuo. The aqueous residue is extracted with 4×100 ml diethyl ether. The organics are combined, dried over magnesium sulfate, and concentrated in vacuo to a purple oil.

The oil is chromatographed over 200 g silica gel (230–400 mesh), eluting with 9% ethyl acetate/hexane and after a 1000 ml forerun collecting 22 ml fractions to separate trans and cis epoxides of the title compound. Following the above procedure gives the title compound having the physical characteristic described below:

TLC (silica gel 60, F-254): Rf (trans)=0.39 (30% ethyl acetate/hexane); Rf (cis)=0.35 (30% ethyl acetate/hexane).

EXAMPLE 21

2H-Pyran-2-one,tetrahydro-6-[[3-(3-hydroxy-5-undecen-1-ynyl)phenyl]methyl]-

3-Hydroxyundec-5Z-ene-1-yne (0.810 g, 4.9 mmole) and 5-(m-bromobenzyl)tetrhydropyran-2-one (1.08 g, 4.0 mmole) are combined in 20 ml degassed triethylamine in an oven dried 50 ml one-neck round bottom flask under argon. The solution is treated with (bis)triphenylphosphinopalladium dichloride (150 mg, 0.213 mmole) and the mixture is immediately heated to reflux. Cuprous iodide (21 mg, 0.110 mmole) is rapidly added to the reaction flask in one lot and the mixture is refluxed for 1.25 hours. The reaction mixture is cooled to room temperature and the volatiles removed in vacuo. The black residue is partitioned between 50 ml 90% saturated ammonium chloride/sodium chloride (1:1) and 50 ml diethyl ether. The aqueous layer is extracted with 4×30 ml diethyl ether. The organics are combined, dried over magnesium sulfate, and concentrated in vacuo to a black oil.

The oil is chromatographed over 105 g silica gel (230–400 mesh), eluting with 10% acetone/hexane for a 2600 ml forerun and then with 15% acetone/hexane while collecting 20 ml fractions. Fractions 19–52 are combined and concentrated to afford 1.01 g of the title compound as a brown oil. Following the above procedure gives the title compound having the physical characteristic described below:

TLC (silica gel 60, F-254): $R_f$=0.50 (60% ethyl acetate/hexane).

EXAMPLE 22

1,5-Hexanediol,6-[3-(3-hydroxy-1,5-undecadienyl)-phenyl]-

Sodium (bis)2-methoxyethoxyaluminum hydride (3.4M/toluene; 1.3 ml, 4.47 mmole) is dissolved in 3 ml dry toluene in an oven dried 25 ml 2-neck round bottom flask under nitrogen at 0° C. The solution is cooled to −78° C. and treated with 5-(3-[3-hydroxy-undec-5Z-en-1-ynyl]phenyl)-methyl-tetrahydropyran-2-one (317 mg, 0.89 mmole) in 4×0.5 ml dry toluene. The reaction mixture is stirred 10 minutes at −78° C., warmed to 0° C., and stirred an additional 4.5 hours. The mixture is quenched at 0° C. with 200 μl water, diluted with 5 ml diethyl ether, and stirred vigorously with 10 ml 0.5M sodium potassium tartrate for one hour. The mixture is extracted with 4×15 ml diethyl ether. The organics are combined, dried over magnesium sulfate, and concentrated in vacuo to a yellow oil (357 mg).

The oil is chromatographed over 15 g silica gel (230–400 mesh), eluting with 35% acetone/hexane and collecting 4 ml fractions. Fractions 15–33 are combined and concentrated to give 292 mg of the title compound as a pale yellow oil. Following the above procedure gives the title compound having the physical characteristic described below:

TLC (silica gel 60, F-254): $R_f$=0.10 (60% ethyl acetate/hexane).

EXAMPLE 23

δ-Hydroxy-3-(3-hydroxy-1,5-undecadienyl)benzenehexanoic acid, and

Tetrahydro-6-[[3-(3-hydroxy-1,5-undecadienyl)-phenyl]methyl]-2H-pyran-2-one

Adams catalyst (85%, 730 mg) is suspended in 160 ml water in a 500 ml 3-neck round bottom flask and prereduced under hydrogen at atmospheric pressure for one hour. The reduced catalyst suspension is subjected to a vigorous nitrogen/vacuum purge (10×) and nitrogen is bubbled through the suspension for 30 minutes via a 16-gauge needle. The nitrogen inlet is replaced with an oxygen inlet and oxygen is continuously bubbled into the reaction mixture. Sodium bicarbonate (0.990 g, 11.8 mmole) is added to the reaction mixture in a single lot. 6-(3-[3-Hydroxy-undec-1E-5Z-dien-1-yl]phenyl)-hexane-1,5-diol (0.418 g, 1.17 mmole), in 4×10.5 ml acetone, is added rapidly to the reaction mixture at room temperature. The reaction is heated to 55° C. for 5 hours and subsequently cooled to room temperature. The reaction mixture is filtered through a one inch bed of celite and the filtrate acidified to pH 3.2 with 0.25M sodium hydrogen sulfate. The mixture is extracted with 1×200 ml diethyl ether followed by 3×100 ml diethyl ether. The organics are combined, dried over magnesium sulfate, and concentrated in vacuo to a crude yellow oil (420 mg).

The oil is chromatographed over 15 g silica gel (230–400 mesh), eluting with 8% methanol/dichloromethane and collecting 3 ml fractions. Fractions 20–54 are combined and concentrated to afford 195 mg of δ-hydroxy-3-(3-hydroxy-1,5-undecadienyl)benzenehexanoic acid. Fractions 8–13 are combined, concentrated, and rechromatographed over 15 g silica gel (230–400 mesh). Elution is carried out with 1.5% methanol/dichloromethane and 3 ml fractions are collected. Fractions 19–33 are combined and concentrated to provide 84 mg of tetrahydro-6-[[3-(3-hydroxy-1,5-undecadienyl)phenyl]methyl]-2H-pyran-2-one as a colorless oil. Following the above procedure gives the title compound having the physical characteristic described below:

TLC (silica gel 60, F-254) acid: $R_f$=0.24 (50% acetone/hexane).

TLC (silica gel 60, F-254) pyran-2-one: $R_f$=0.78 (50% acetone/hexane).

EXAMPLE 24

Benzenehexanoic acid, delta-hydroxy-3-[(3-hydroxy-5-undecen-1-ynyl)]

5(3-[3-Hydroxy-undec-1E-5Z-dien-1-yl]phenyl)-tetrahydropyran-2-one (102 mg, 0.288 mmole) is dissolved in 12 ml methanol in a 100 ml one-neck round bottom flask. The solution is diluted with 3 ml water and treated with 0.5N sodium hydroxide (7.5 ml, 3.75 mmole). The reaction mixture is stirred 30 minutes at room temperature. The methanol is removed in vacuo and the pH of the aqueous residue is adjusted to 3.5 with 0.25M sodium hydrogen sulfate. The mixture is extracted with 4×10 ml diethyl ether. The organics are combined, dried over magnesium sulfate, and concentrated in vacuo to provide 105 mg of the title compound as a pale yellow oil. The product is stable as a methanol solution. Following the above procedure gives the title compound having the physical characteristic described below:

TLC (silica gel 60, F-254): $R_f$=0.17 (50% acetone/hexane).

EXAMPLE 25

5,6-Epoxy-6-(3-[3-hydroxy-undec-5Z-en-1-ynyl]phenyl) hexanoic acid methyl ester

3-Hydroxy-undec-5Z-ene-1-yne (0.115 g, 0.69 mmole) and 6-(3-bromophenyl-5-6-epoxy-hexanoic acid (0.172 g, 0.58 mmole) are combined in 2.5 ml degassed triethylamine in an oven dried 25 ml one-neck round bottom flask under argon. The solution is treated with (bis)triphenylphosphinopalladium dichloride (8 mg, 0.012 mmole) in a single lot at room temperature. The mixture is immediately heated to reflux and treated with cuprous iodide (1.4 mg, 0.007 mmole) in a single lot. The reaction mixture is refluxed for 1.25 hours and cooled to room temperature. The volatiles are removed in vacuo and the black residue taken up in 15 ml diethyl ether. The ether layer is washed with 15 ml 90% saturated ammonium chloride/sodium chloride (1:1). The aqueous layer is washed with 3×10 ml diethyl ether. The organics are combined, dried over magnesium sulfate, and concentrated in vacuo to a dark brown oil (257 mg).

The oil is chromatographed over 10.6 g silica gel (230–400 mesh), eluting with 20% ethyl acetate/hexane and collecting 4 ml fractions. Fractions 13–24 are combined and concentrated to afford 163 mg of the title compound as a light amber oil. Following the above procedure gives the title compound having the physical characteristic described below:

TLC (silica gel 60, F-254): $R_f$=0.28 (30% ethyl acetate/hexane).

EXAMPLE 26

Oxiranebutanol,
3-[3-(3-hydroxy-1,5-undecadienyl)phenyl]-

Sodium (bis)-2-methoxyethoxyaluminum hydride (3.4M/toluene; 0.78 ml, 2.65 mmole) is dissolved in 12 ml dry toluene in an oven dried 50 ml 2-neck round bottom flask under nitrogen at 0° C. 5,6-Epoxy-6-(3-[3-hydroxy-undec-5Z-en-1-ynyl]phenyl) hexanoic acid methyl ester (300 mg, 0.78 mmole) in 3×1 ml dry toluene, is added slowly dropwise to the reaction mixture at 0° C. The reaction is stirred 4.5 hours at 0° C., quenched with 400 L water, and stirred vigorously with 25 ml 0.5M sodium potassium tartrate and 10 ml diethyl ether for one hour. The mixture is extracted with 4×15 ml diethyl ether. The organics are combined, dried over magnesium sulfate, and concentrated in vacuo to a yellow oil (310 mg).

The oil is chromatographed over 10 g silica gel (230–400 mesh), eluting with 50% ethyl acetate/hexane and collecting 4 ml fractions. Fractions 11–24 are combined and concentrated to afford 270 mg of the title compound as a pale yellow oil. Following the above procedure gives the title compound having the physical characteristic described below:

TLC (silica gel 60, F-254): $R_f=0.10$ (40% ethyl acetate/hexane).

EXAMPLE 27

Oxiranebutanoic acid,
3-[3-(3-hydroxy-1,5-undecadienyl)phenyl]-

Adams catalyst (354 mg) is suspended in 70 ml high purity water and prereduced under ambient hydrogen atmosphere for one hour. The reduced catalyst suspension is subjected to a thorough nitrogen/vacuum purge (10×) and transferred to a 250 ml 3-neck round bottom flask. The suspension is stirred 30 minutes at room temperature as nitrogen is bubbled in via a 16-gauge needle. After 30 minutes, the nitrogen inlet is replaced with an oxygen inlet and oxygen is continuously bubbled into the reaction mixture. Sodium bicarbonate (469 mg, 5.58 mmole) is added to the reaction mixture in a single lot. 5,6-epoxy-6-(3-[3-hydroxy-undec-1E,5Z-dien-1-yl]phenyl) hexane-1-ol (203 mg, 0.566 mmole), in 2×10 ml acetone, is added rapidly to the reaction mixture at room temperature. The reaction is heated to 55° C. for one hour, cooled to room temperature, and the pH carefully adjusted to 4 with 0.25M sodium hydrogen sulfate. The mixture is extracted with 1×60 ml diethyl ether followed by 3×20 ml diethyl ether. The organics are combined, filtered through a one inch bed of celite, and dried over magnesium sulfate. The organics are concentrated in vacuo to a pale yellow oil (237 mg). The oil is chromatographed over 16 g silica gel (230–400 mesh), eluting with 4% methanol/dichloromethane, and collecting 3 ml fractions. Fractions 25–69 are combined and concentrated to afford 86 mg of the title compound. Following the above procedure gives the title compound having the physical characteristic described below:

TLC (silica gel 60, F-254): $R_f=0.21$ (50% ethyl acetate/hexane).

EXAMPLE 28

6-Bromo-2-formyl-pyridine 2,6-Dibromopyridine (25 g, 0.105 mol) is suspended in 200 ml of ether. The solution is cooled to −78° C. and n-butyllithium (65.6 ml, 1.6M, 0.105 mol) in hexane is added slowly dropwise over a 1.5 hour period. After 5 minutes, dimethylformamide (8.4 g, 0.115 mol) in 13 ml of ether is added slowly dropwise over one hour. The reaction is allowed to stir at −78° C. for 1.5 hours. The mixture is warmed to −25° C. and 40 ml of 6N hydrochloric acid is added. The mixture is allowed to warm to room temperature. The aqueous phase is extracted three times with ether and the combined organics are washed once with water, dried over sodium sulfate and evaporated. Trituration with pentane afforded 15.0 g of the title compound as a tannish-white solid.

$^1$H-NMR (CDCl$_3$, TMS): 8.13–7.73; 10.13.

EXAMPLE 29

6-(6-Bromopyridine-2-yl)-5 hexenoic acid

4-Carboxybutyl triphenylphosphonium bromide (29.5 g, 66 mmole) is suspended in 125 ml dry THF in a flame dried 1,000 ml 3-neck round bottom flask under nitrogen. The suspension is treated slowly dropwise with lithium (bis) trimethylsilyl amide (1.0M, THF; 125 ml, 125 mmole) over 30 minutes at room temperature. The resulting red ylid is stirred one hour at room temperature. 6-Bromo-2-formylpyridine (10.5 g, 56.6 mmole), in 1×35 ml dry THF (10 ml rinse), is added slowly dropwise to the reaction mixture over 15 minutes. The brown mixture is stirred at ambient temperature overnight. The reaction is quenched with 100 ml water and the THF removed in vacuo. The aqueous residue is extracted with 3×70 ml diethyl ether. The organics are combined and back extracted with 3×50 ml water. The aqueous layers are combined and the pH adjusted to 4 with 5% hydrochloric acid. The mixture is extracted with 3×100 ml ethyl acetate, the pH of the aqueous phase readjusted to 4, and further extracted with 2×100-ml ethyl acetate. The organics are combined, dried over magnesium sulfate, and concentrated in vacuo to an amber oil.

The oil is chromatographed over 400 g silica gel (230–400 mesh), eluting with 20% acetone/hexane and following a 1,500 ml forerun collecting 60 ml fractions. Fractions 18–53 are combined and concentrated to afford 9.6 g of a 4:1 cis/trans mixture of the title compound as a yellow oil.

The mixture (5.0 g, 18.5 mmole) is dissolved in 30 ml dichloromethane in a 250 ml one-neck round bottom flask. This solution is slurried with 10 g silica gel (230–400-mesh) and the dichloromethane removed in vacuo, effectively adsorbing the solute onto the silica gel. This material is chromatographed over 290 g silica gel (230–400 mesh), eluting with 15% acetone/hexane and following a 2,000 ml forerun collecting 50 ml fractions. Fractions 15–39 are combined and concentrated to afford 2.7 g of the title compound as a yellow oil.

TLC (silica gel 60, F-254): $R_f=0.62$ (50% acetone/hexane).

EXAMPLE 30

6-([6-Bromopyridine-2-yl)]-iodomethyl)tetrahydropyran-2-one 6-(6-Bromopyridine-2-yl)-5 hexenoic acid (830 mg, 3.07 mmole) is dissolved in 12 ml dry THF in a 50 ml one-neck round bottom flask under nitrogen. The solution is diluted with 6 ml water and treated with potassium bicarbonate (350 mg, 3.5 mmole). The mixture is stirred 30 minutes at room temperature and cooled to 0°

C. Potassium iodide (2.28 g, 13.7 mmole) and iodine (6.9 g, 27.2 mmole) are added successively portionwise to the reaction mixture at 0° C. The reaction is stirred at room temperature overnight. The mixture is diluted with 20 ml saturated sodium thiosulfate and then treated portionwise with solid sodium thiosulfate until the excess iodine is consumed and the reaction mixture is pale yellow. The THF is removed in vacuo and the aqueous residue is extracted with 4×25 ml ethyl acetate. The organics are combined, dried over magnesium sulfate and concentrated in vacuo to afford 1.10 g of the title compound as a pale orange solid. Following the above procedure gives the title compound having the physical characteristic described below:

TLC (silica gel 60, F-254): Rf=0.56 (50% acetone/hexane).

EXAMPLE 31

6-(6-Bromopyridine-2-yl)methyl-tetrahydropyran-2one 6-([6-Bromopyridine-2-yl)]-iodomethyl)tetrahydropyran-2-one (4.26 g, 10.76 mmol) is dissolved in 44 ml of toluene under nitrogen. Tri-n-butyltin hydride (3.34 ml, 11.84 mmol) is added followed by azo-bis(isobutyrylnitrile) (176 mg, 1.07 mmol) and the reaction is heated at 75° C. for one hour. The mixture is allowed to cool and partitioned between acetonitrile and hexane. The acetonitrile layer is washed four times with hexane. The combined hexane layers are extracted once with acetonitrile. The new acetonitrile layer is washed four times with hexane. The combined acetonitrile layers are evaporated and the crude material is chromatographed on silica gel (230–400 mesh) eluting with 50% ethyl acetate/hexane. Recrystallization from ether-hexne afforded 1.73 g of the title compound. Following the above procedure gives the title compound having the physical characteristic described below:

$^1$H-NMR (CDCl$_3$, TMS): 1.2–2.2; 2.3–2.65; 3.10; 4.65–5.0; 7.18–7.65.

EXAMPLE 32

6-(6-Bromopyridine-2-yl)-5,6-expoxy hexanoic acid methyl ester 6-([6-Bromopyridine-2-yl)]-iodomethyl)tetrahydropyran-2-one (1.10 g, 2.89 mmole) is dissolved in 25 ml methanol in a 100 ml one-neck round bottom flask. The solution is treated with solid potassium carbonate (800 mg, 5.77 mmole) and the mixture is stirred one hour at room temperature. The reaction is diluted with 20 ml 80% saturated sodium chloride and the excess methanol removed in vacuo. The aqueous residue is extracted with 4×20 ml diethyl ether. The organics are combined, dried over magnesium sulfate, and concentrated in vacuo to a pale oil (713 mg).

The oil is chromatographed over 35 g silica gel (230–400 mesh), eluting with 30% ethyl acetate/hexane and collecting 8 ml fractions. Fractions 16-32 are combined and concentrated to provide 695 mg of the title compound as a colorless oil. Following the above procedure gives the title compound having the physical characteristic described below:

TLC (silica gel 60, F-254): R$_f$=0.30 (30% ethyl acetate/hexane).

EXAMPLE 33

2H-Pyran-2-one, tetrahydro-6-[[6-(3-hydroxy-5-undecen-1-ynyl)-2-pyridinyl]methyl]-

3-Hydroxy-undec-5Z-en-1-yne (800 mg, 4.8 mmole) and 6-(6-bromopyridine-2-yl)methyl-tetrahydropyran-2-one (1.08 g, 4 mmole) are combined in 20 ml degassed triethylanine in a 50 ml one-neck round bottom flask under argon. The mixture is treated with (bis)triphenylphosphine palladium dichloride (60 mg, 0.085 mmole), warmed to 50° C., and treated with cuprous iodide (8 mg, 0.43 mmole). The reaction mixture is stirred for 2 hours at 50° C., cooled to room temperature, and the volatiles removed in vacuo. The residue is partitioned between 20 ml 80% saturated sodium chloride and 20 ml diethyl ether. The organics are combined, dried over magnesium sulfate, and concentrated in vacuo to a brown oil.

The oil is chromatographed over 50 g silica gel (230–400 mesh), eluting with 65% ethyl acetate/hexane and collecting 16 ml fractions. Fractions 12-36 are combined and concentrated to afford 1.41 g of the title compound as a pale amber oil. Following the above procedure gives the title compound having the physical characteristic described below:

TLC (silica gel 60, F-254): R$_f$=0.40 (50% acetone/hexane).

EXAMPLE 34

1,5-Hexanediol, 6-[6-(3-hydroxy-undecadienyl)-2-pyridinyl]-

Sodium (bis)2-methoxyethoxy-aluminum hydride (3.4-M, toluene; 2.9 ml, 10 mmole) is dissolved in 15 ml dry toluene in an oven dried 50 ml 2-neck round bottom flask under nitrogen at 0° C. 5-(6-[3-Hydroxy-undec-5Z-en-1-yn-yl]pyridine-2-yl)methyl-tetrahydropyran-2-one (711 mg, 2 mmole), in 3×1 0.5 ml dry toluene, is added slowly dropwise to the reaction mixture at 0° C. The reaction is stirred 20 minutes at 0° C. The reaction is stirred 20 minutes at 0° C., warmed to room temperature, and stirred for 3 hours. The reaction is quenched by the careful addition of 400 ml water. The mixture is diluted with 10 ml 0.5M sodium potassium tartrate and 10 ml diethyl ether and stirred vigorously over night. The mixture is poured into 1×10 ml saturated sodium chloride and extracted with 4×20 ml diethyl ether. The organics are combined, dried over magnesium sulfate, and concentrated in vacuo to a pale oil. The oil is chromatographed over 30 g silica gel (230–400 mesh) eluting with 30% acetone/hexane and collecting 16 ml fractions. Fractions 16-26 are combined and concentrated to afford 520 mg of the title compound as a pale oil. Following the above procedure gives the title compound having the physical characteristic described below:

TLC (silica gel 60, F-254): Rf=0.27 (50% acetone/hexane).

EXAMPLE 35

2-Pyridinehexanoic acid, delta-hydroxy-6-(3-hydroxy-1,5-undecadienyl) -

Adams catalyst (895 mg) is suspended in 160 ml water in a 250 ml one-neck round bottom flask and stirred under hydrogen atmosphere for one hour. The reduced catalyst suspension is subjected to a vigorous vacuum/ nitrogen purge (10×) and nitrogen is bubbled through the mixture for 30 minutes via a 16-gauge needle. After 30 minutes the nitrogen inlet is replaced with an oxygen inlet and oxygen is continuously bubbled into the reaction mixture. The mixture is treated with sodium bicarbonate (1.2 g, 14.3 mmole) followed by 6-(6-[3-hydroxy-undec-1E,5Z-dien-1-yl]pyridine-2-yl)-hexane-1,5-diol (518 mg, 1.43 mmole) in 4×10 ml acetone. The reaction is heated to 50° C. for 4 hours, the reaction is cooled to room temperature and the majority of the acetone removed in vacuo. The pH of the aqueous residue is adjusted to 35 with 2M sodium hydrogen sulfate. The mixture is extracted with 4×30 ml ethyl acetate. The organics are combined, dried over magnesium sulfate, and concentrated in vacuo to a pale oil (500 mg). The oil is chromatographed over 15 g silica gel (230–400 mesh), eluting with 8% methanol/dichloromethane and collecting 3 ml fractions. Fractions 16–36 are combined and concentrated to afford 71 mg of the title compound as an unstable oil which is stored as a stable methanol solution. Following the above procedure gives the title compound having the physical characteristic described below:

TLC (silica gel 60, F-254): $R_f = 0.13$ (10% methanol/dichloromethane).

EXAMPLE 36

2-Pyridinehexanoic acid, delta-hydroxy-6-(3-hydroxy-5-undecen-1-ynyl) -

5-[6-[3-Hydroxy-undec-5Z-en-1-yn-yl]pyridine-2-yl]methyl-tetrahydropyran-2-one (72 mg, 0.202 mmole) is dissolved in 6 ml methanol in a 25 ml one-neck round bottom flask. The solution is diluted with 1.5 ml water and treated with 0.5N sodium hydroxide (3.5 ml, 1.75 mmole). The reaction mixture is stirred one hour at room temperature. The methanol is removed in vacuo and the pH of the aqueous residue is adjusted to 3 with 0.25M sodium hydrogen sulfate. The aqueous layer is thoroughly extracted with 4×10 ml diethyl ether. The organics are combined, dried over magnesium sulfate, and concentrated in vacuo to afford 71 mg of the title compound as an unstable pale oil. The compound is stored as a methanol solution. Following the above procedure gives the title compound having the physical characteristic described below:

TLC (silica gel 60, F-254): Rf=0.27 (10% methanol/dichloromethane).

EXAMPLE 37

5-Hexenoic acid, 6-[6-(3-hydroxy-5-undecen-1-ynyl)-2-pyridinyl], (Z,Z)-

3-Hydroxy-undec-5Z-ene-1-yne (206 mg, 1.24 mmole) and 6-(6-bromopyridine-2-yl)-5 hexenoic acid (280 mg, 1.04 mmole) are combined in 2 ml degassed triethylanine in a 25 ml one-neck round bottom flask under argon. The mixture is treated with (bis)triphenylphosphine palladium dichloride (15 mg, 0.021 mmole), warmed to 50° C., and subsequently treated with cuprous iodide (2 mg, 0.011 mmole) in a single lot. The reaction is stirred 4 hours at 50° C. and cooled to room temperature. The volatiles are removed in vacuo and the black residue is taken up in 10 ml 80% saturated ammonium chloride. The pH is adjusted to 3.5 with 0.25M sodium hydrogen sulfate and the aqueous mixture extracted with 4×10 ml ethyl acetate. The organics are combined, dried over magnesium sulfate, and concentrated in vacuo to a dark brown oil (410 mg). The oil is chromatographed over 12 g silica gel (230–400 mesh), eluting with 3% methanol/dichloromethane and collecting 3 ml fractions. Fractions 16–54 are combined and concentrated to give 232 mg of the title compound as a pale amber oil. Following the above procedure gives the title compound having the physical characteristic described below:

TLC (silica gel 60, F-254): $R_f = 0.13$, (5% methanol/dichloromethane).

EXAMPLE 38

1,5-Undecadien-3-ol, 1-[6-(6-hydroxy-1-hexenyl)-2-pyridinyl]-. (E,Z,Z)-

Sodium (bis)2-methoxyethoxy aluminum hydride (3.4M, toluene; 1 ml, 3.4 mmole) is dissolved in 8 ml dry toluene in an oven dried 50 ml 2-neck round bottom flask under nitrogen at 0° C. 6-(6-[3-Hydroxy-undec-5Z-ene-1-ynyl]pyridine-2-yl)-5Z hexanoic acid (232 mg, 0.652 mmole), in 3×1 ml dry toluene, is added dropwise to the reaction mixture at 0° C. The reaction mixture is stirred 3 hours at 0° C., quenched with 400 ml water, and stirred vigorously with 10 ml 0.5M sodium potassium tartrate for one hour. The mixture is poured into 10 ml saturated sodium chloride, the layers separated, and the aqueous layer extracted with 4×10 ml diethyl ether. The organics are combined, dried over magnesium sulfate, and concentrated in vacuo to a crude oil. The oil is chromatographed over 11.5 g silica gel (230–400 mesh), eluting with 50% ethyl acetate/hexane and collecting 3 ml fractions. Fractions 16–26 are combined and concentrated to afford 150 mg of the title compound as a light oil. Following the above procedure gives the title compound having the physical characteristic described below:

TLC (silica gel 60, F-254): $R_f = 0.32$ (60% ethyl acetate/hexane).

EXAMPLE 39

5-Hexenoic acid, 6-[6-(3-hydroxy-1,5-undecadienyl)-2-pyridinyl]-, (E,Z,Z)-

Adams catalyst (275 mg) is prereduced by stirring in 40 ml water in a 100 ml 3-neck round bottom flask under a hydrogen atmosphere for one hour. The reduced catalyst suspension is subjected to a vigorous nitrogen/vacuum purge (10X) and nitrogen is bubbled into the mixture via a 16-gauge needle for 30 minutes. After 30 minutes, the nitrogen inlet is replaced with an oxygen inlet and oxygen is continuously bubbled into the reaction mixture. The mixture is treated with sodium bicarbonate (375 mg, 4.4 mmole) followed by 6-(6-[3-hydroxy-undec-1E,5Z-dien-1-yl]pyridine-2-yl)-5Z-hexen-1-ol (150 mg, 0.44 mmole) in 4×2.5 ml acetone. The reaction mixture is heated to 50° C. for 5.5 hours, cooled to 0° C., and the catalyst separated by filtration through a one inch bed of celite. The celite is washed with 70 ml acetone and the filtrate concentrated in vacuo to primarily an aqueous residue. The pH of the residue is adjusted to 3.75 with 2M sodium hydrogen sulfate. The mixture is extracted with 4×20 ml diethyl ether. The organics are combined, dried over magnesium sulfate, and concentrated in vacuo to a yellow oil (145 mg). The oil is chromatographed over 6.5 g silica gel (230–400 mesh), eluting with 3% methanol/dichloromethane and collecting 2 ml fractions. Fractions 17–54 are combined and concentrated to afford 94 mg of the title compound as a viscous oil.

Following the above procedure gives the title compound having the physical characteristic described below:

TLC (silica gel 60, F-254): $R_f$=0.46 (10% methanol/dichloromethane).

EXAMPLE 40

5,6-Epoxy-6-(6-[3-Hydroxy-undec-5Z-ene-1-ynyl]pyridine-2-yl) hexanoic acid methyl ester 3-Hydroxyundec-5Z-en-1-yne (200 mg, 1.2 mmole) and 6-(6-bromopyridine-2-yl)-5,6-expoxy hexanoic acid methyl ester (2.96 mg, 0.986 mmole) are combined in 2 ml degassed triethylamine in a 25 ml one-neck round bottom flask under argon. The mixture is treated with (bis)triphenylphosphine palladium dichloride (14 mg, 0.02 mmole), warmed to 50° C., and treated with cuprous iodide (2 mg, 0.01 mmole) in one lot. The reaction mixture is stirred 1.5 hours at 50° C., cooled to room temperature, and the volatiles removed in vacuo. The residue is dissolved in 15 ml diethyl ether and washed with 1×15 ml 80% saturated ammonium chloride/sodium chloride (1:1). The layers are separated and the aqueous layer is back washed with 3×10 ml diethyl ether. The organics are combined, dried, over magnesium sulfate, and concentrated in vacuo to a light brown oil (427-mg). The oil is chromatographed over 15 g silica gel (230–400 mesh) eluting with 45% acetone/hexane and collecting 4 ml fractions. Fractions 11–27 are combined and concentrated to provide 368 mg of title compound as a light yellow oil. Following the above procedure gives the title compound having the physical characteristic described below:

TLC (silica gel 60, F-254): $R_f$=0.40 (60% ethyl acetate/hexane).

EXAMPLE 41

Oxiranebutanol, 3-[6-(3-hydroxy-1,5-undecadienyl)-2-pyridinyl]-

Sodium (bis)2-methoxyethoxy aluminum hydride (3.4M, toluene; 1.4 ml, 4.77 mmole) is dissolved in 8 ml dry toluene in an oven dried 50 ml 2-neck round bottom flask under nitrogen at 0° C. 5,6-Epoxy-6-(6-[3-hydroxy-undec-5Z-ene-1-ynyl]pyridine-2-yl) hexanoic acid methyl ester (368 mg, 0.95 mmole), in 2×1 ml dry toluene, is added slowly dropwise to the reaction mixture at 0° C. The reaction is stirred at 0° C. for 4 hours, quenched with 300 ml water, and stirred vigorously with 10 ml 0.5M sodium potassium tartrate for 2 hours. The mixture is extracted with 4×10 ml diethyl ether. The organics are combined, dried over magnesium sulfate, and concentrated in vacuo to a pale oil (365 mg). The oil is chromatographed over 14 g silica gel (230–400 mesh), eluting with 70% ethyl acetate/hexane and collecting 4 ml fractions. Fractions 16–33 are combined and concentrated to give 221 mg of the title compound as a colorless oil. Following the above procedure gives the title compound having the physical characteristic described below:

TLC (silica gel 60, F-254): $R_f$=0.14 (60% ethyl acetate/hexane).

EXAMPLE 42

Pxoramebitampoc acod. 3-[6-(3-hydroxy-1,5-undecadienyl)-2-pyridinyl]-

Adams catalyst (385 mg) is prereduced by stirring in a hydrogen atmosphere for one hour while suspended in 40 ml water in a 100 ml 2-neck round bottom flask. The reduced catalyst suspension is subjected to a vigorous nitrogen/vacuum purge (10×) and nitrogen is bubbled through the mixture for 30 minutes via a 16-guage needle. After 30 minutes the nitrogen inlet is replaced with an oxygen inlet and oxygen is continuously bubbled into the reaction mixture. The suspension is treated with sodium bicarbonate (490 mg, 5.84 mmole) followed by 5,6-epoxy-6(6-[3-Hydroxy-undec-1E,5Z-dien-1-yl]pyridine-2-yl)hexane-1-ol (210 mg, 0.584 mmole) in 2×4 ml acetone. The reaction mixture is heated to 55° C. for one hour, cooled to 0° C., and filtered through a one inch bed of celite. The filter cake is washed with 30 ml 30% acetone/water. The filtrate is acidified to pH=3.5 with 0.25M sodium hydrogen sulfate and the mixture extracted with 4×30 ml diethyl ether. The organics are combined, dried over magnesium sulfate, and concentrated in vacuo to a pale oil (196 mg). The oil is chromatographed over 12 g silica gel (230–400 mesh), eluting with 45% acetone hexane and collecting 3 ml fractions. Fractions 11–42 are combined and concentrated to afford 116 mg of the title compound as a pale oil.

EXAMPLE 43

D-Mannitol triacetonide

D-Mannitol (235.6 g, 1.29 mole) is suspended in a solution of acetone (2 L) and concentrated sulfuric acid (16 ml) in a 5 L 3-neck round bottom flask equipped with a mechanical stirrer. The reaction mixture is stirred 6 hours at room temperature. The solid residue is removed by filtration (32.6 g) and the filtrate is poured into 500 ml 1.2N sodium hydroxide at 0° C. The pH of the mixture is adjusted to 7.5 with 3N sodium hydroxide (pH meter) and the acetone is removed in vacuo. The heavy aqueous slurry is chilled overnight. The solid is collected on a suction filter and the filter cake is washed well with 300 ml water. Most of the water is removed via filtration and the filter cake is dissolved in 500 ml hot 95% ethanol. The first crop of crystals forms on standing at room temperature. The crystals are filtered off, washed with 200 ml fresh cold 95% ethanol, and dried in vacuo at 25° C. to provide 121.1 g of the title compound. The mother liquor is chilled to −10° C. for 2 hours to provide a second crop of crystals which upon drying in vacuo at 25° C. provide an additional 64.9 g.

Melting point: 68.5°-69.5° C. Optical rotation: $[\alpha]_D$=+15.0°; (CHCl$_3$, c=0.982). Mass spectrum: Calculated for $C_{15}H_{26}O_6$: 302.1729; found: 302.1726.

EXAMPLE 44

Mannitol-3,4-acetonide

D-Mannitol triacetonide (55.54 g, 184 mmol) is dissolved in 1000 ml 70% aqueous acetic acid in a 2000 ml one-neck round bottom flask equipped with an air condenser. The reaction mixture is warmed to 40° C. for 2 hours and the acetic acid/water is removed rapidly in vacuo at 50°-60° C. The white residue is triturated with acetone and the mannitol filtered off (4.0 g, 12%). The filtrate, upon chilling, yields 23.1 g of the title compound. The mother liquor is concentrated in vacuo to a heavy syrup which crystallizes on standing. The material is dissolved in 10 ml acetone, diluted with 90 ml benzene, and chilled thoroughly. The resulting crystalline sold is filtered off and after drying in vacuo at 25° C. provides an additional 8.9 g.

Melting point: 83.5°-4.9° C. Optical rotation: $[\alpha]_D$=+17.6°; (pyridine, c=0.592). Mass spectrum: Calculated for $C_9H_{18}O_6$: 222.1103; found: 222.1112.

EXAMPLE 45

1.6-Ditosyl-Mannitol-3,4-acetonide

Mannitol-3,4-acetonide (22.9 g, 103.3 mmole) is dissolved in 300 ml dry pyridine in a flame dried 1000 ml 3-neck round bottom flask under nitrogen. The solution is cooled to 0° C. and treated slowly dropwise with freshly recrystallized tosyl chloride (40.4 g, 211.8 mmole) in 100 ml dry pyridine. The reaction mixture is stirred 5 hours at 0° C., placed under argon, and refrigerated overnight. The mixture is warmed to room temperature and the pyridine is removed in vacuo at 50° C. (bath). The residue is dissolved in 500 ml ethyl acetate and washed successively with 1×250 ml water, 3×250 ml 1N hydrochloric acid, 1×150 ml saturated cupric sulfate, 1×150 ml saturated sodium chloride and 1×150 ml saturated sodium bicarbonate. The organics are dried over magnesium sulfate and concentrated in vacuo to a heavy pale syrup. An aliquot of the syrup (2.3 g) is chromatographed over 90 g silica gel (230–400 mesh), eluting with 40% ethyl acetate/hexane and collecting 20 ml fractions. Fractions 72–95 are combined and concentrated to provide 1.48 g of the ditosylate as a colorless oil. The oil is layered with 1:1 diethyl ether/light petroleum ether and provides a white crystalline solid. The bulk of the oil is seeded with the pure crystals and layered with 1:1 diethyl ether/light petroleum ether. The mixture is allowed to stand for 48 hours. The supernatant is removed in vacuo, and the heavy paste is slurried successively with hexane and diethyl ether. The resulting white solid is collected by filtration to provide 23.1 g of the title compound.

Melting point: 107°–108.5° C. Optical rotation: $[\alpha]_D = +27.1°$; (CHCl$_3$, c=0.756).

EXAMPLE 46

2,2-Dimethyl-4,5-(oxirane-2R-yl)-1S,3R-dioxolane 1.6-Ditosyl-Mannitol-3,4-acetonide (16.53 g, 31.2 mmole) is combined with potassium carbonate (17.22 g, 125 mmole) in 150 ml methanol in a 500 ml one-neck round bottom flask under nitrogen. The reaction mixture is stirred one hour at room temperature. The solids are removed by filtration and the filtrate is concentrated in vacuo to a slurry of salts. The residue is suspended in 200 ml ethyl acetate and the solids removed via filtration through an 8 g plug of silica gel (230–400 mesh). The filtrate is concentrated in vacuo to provide 5.54 of the title compound.

Optical rotation: $[\alpha]_D = -1.6°$; (CHCl$_3$, c=0.7025). Mass spectrum: M/$_z$ (Relative Intensity); [M-CH$_3$]$^+$ = 171 (80).

EXAMPLE 47

2,2-Dimethyl-4,5-[1R-benzoyloxy-non-3yn-1yl]-1S,3R-dioxolane

1-Heptyne (8.20 ml, 62.48 mmole) is dissolved in 75 ml dry tetrahydrofuran in an oven dried 250 ml 3-neck round bottom flask under nitrogen. The mixture is cooled to 0° C., treated with n-butyllithium (40.3 ml, 62.48 mmole) slowly dropwise and stirred 15 minutes at 0° C. The reaction mixture is treated rapidly dropwise with hexamethylphosphoric triamide (11.5 ml) at 0° C. and the mixture is stirred an additional 10 minutes. 2,2-Dimethyl-4,5-(oxirane-2R-yl)-1S,3R-dioxolane (5.54 g, 29.75 mmole) in 3×10 ml dry tetrahydrofuran is added dropwise to the reaction mixture at 0° C. The mixture is warmed to 60° C. and stirred for 3 hours. The reaction mixture is subsequently cooled to 0° C. and treated with benzoyl chloride (7.25 ml, 62.48 mmole) dropwise. The reaction is stirred overnight at +4° C. and an additional 4 hours at room temperature. The mixture is poured into 400 ml saturated sodium bicarbonate and extracted with 4×100 ml ethyl acetate. The combined organics are concentrated in vacuo to an oily residue, dissolved in 150 ml diethyl ether, and washed successively with 3×100 ml half saturated sodium chloride and 1×100 ml saturated sodium chloride. The organic layer is dried over magnesium sulfate and concentrated in vacuo to a heavy amber oil.

The oil is chromatographed over 400 g silica gel (230–400 mesh), eluting with 7% ethyl acetate/hexane and collecting 60 ml fractions. Fractions 20–31 are combined and concentrated to provide 12.31 g of the title compound.

Optical rotation: $[\alpha]_D = +5.0°$; (CH$_2$Cl$_2$, c=1.07). Mass spectrum: M/$_z$ (Relative Intensity); [M-CH$_3$]$^+$ = 571 (10).

EXAMPLE 48

9R,12R-Dibenzoyloxy-10S,11R-dihydroxy-eicosa-6,14-diyne 2,2-Dimethyl-4,5-[1R-benzoyloxy-non-3yn-1yl]-1S,3R-dioxolane (510 mg, 0.866 mmole) is dissolved in 2 ml 70% trifluoroacetic acid in a 50 ml one-neck round bottom flask at 0° C. The reaction mixture is stirred 24 hours at 0°–5° C. The trifluoroacetic acid is neutralized with saturated sodium bicarbonate and the mixture extracted with 3×15 ml ethyl acetate. The combined organics are washed successively with 2×10 ml saturated sodium bicarbonate and 1×10 ml saturated sodium chloride. The organics are dried over magnesium sulfate and concentrated in vacuo to a yellow oil (476 mg).

The oil is chromatographed over 25 g silica gel (230–400 mesh), eluting with 15% ethyl acetate/hexane and collecting 6 ml fractions. Fractions 27–54 are combined and concentrated to afford 326 mg (70%) of the diol as a pale yellow oil. Fractions 6–12 are combined and concentrated to give 62 mg of the title compound.

Optical rotation: $[\alpha]_D = -1.6°$; (CHCl$_3$, c=0.7335). Mass spectrum: Calculated for C$_{34}$H$_{42}$O$_6$: 547.3059; found: 547.3071.

EXAMPLE 49

9R,12R-Dibenzoyloxy-10S,11R-dihydroxy-eicosa-6Z,14Z-diene 9R,12R-Dibenzoyloxy-10S,11R-dihydroxy-eicosa-6,14-diyne (4.94 g, 9.2 mmole) is dissolved in 80 ml benzene in a 200 ml one-neck round bottom flask. The solution is treated with 650 mg 5% palladium on calcium carbonate. The mixture is hydrogenated at atmospheric pressure until 102% of the theoretical amount of hydrogen has been taken up (210 ml). The reaction mixture is filtered through a one-inch bed of celite and the celite is washed with fresh benzene. The filtrate is collected and concentrated to a pale yellow oil.

The oil is chromatographed over 200 g silica gel (230–400 mesh), eluting with 13% ethyl acetate/hexane and collecting 60 ml fractions. Fractions 34–43 are combined and concentrated to afford 386 mg of the title compound.

Optical rotation: $[\alpha]_D = +33.5°$; (CH$_2$Cl$_2$, c=0.902). Mass spectrum: Calculated for C$_{34}$H$_{46}$O$_6$: 551.3372; found: 551.3357.

EXAMPLE 50

2R-Benzoyloxy-4Z-decen-al 9R,12R-Dibenzoyloxy-10S,11R-dihydroxy-eicosa-6Z,14Z-diene (3.32 g, 6.03 mmole) is dissolved in 60 ml dry dichloromethane in a flame dried 250 ml one-neck round bottom flask under nitrogen. The solution is cooled to 0° C. and treated successively portionwise with sodium bicarbonate (5.06 g, 60.3 mmole) and lead tetraacetate (5.23 g, 12.06 mmole). The reaction mixture is quenched with 1×60 ml water and filtered through a one-inch bed of celite. The celite is washed with fresh dichloromethane. The organic layer is washed successively with 2×50 ml saturated sodium bicarbonate and 1×50 ml saturated sodium chloride. The organics are dried over magnesium sulfate and concentrated in vacuo to afford 2.83 g of the title compound as a colorless oil.

To obtain an analytical sample, 250 mg of the title compound is chromatographed over 15 g silica gel (230–400 mesh), eluting with 15% ethyl acetate/hexane and collecting 4 ml fractions. Fractions 11–24 are combined and concentrated to afford 240 mg of the title compound.

Optical rotation: $[\alpha]_D = +14.6°$; ($CH_2Cl_2$, c=1.4). Mass spectrum: M/$_z$ (Relative Intensity); $[M+H]^+ = 275$ (100).

EXAMPLE 51

3R-Benzoyloxy-1-chloro-undec-1,5Z-diene

Chloromethyl triphenylphosphonium chloride (5.14 g, 14.8 mmole) is suspended in 40 ml dry tetrahydrofuran in an oven dried 100 ml 2-neck round bottom flask under nitrogen. The suspension is cooled to 0° C. and treated slowly dropwise with n-butyllithium (9.0 ml, 14.06 mmole). The red ylid is stirred 30 minutes at 0° C. and treated slowly dropwise with 2R-benzoyloxy-4Z-decen-al (2.03 g, 7.4 mmole) in 3×5 ml dry tetrahydrofuran. The reaction mixture is stirred one hour at 0° C., quenched with 40 ml saturated sodium chloride, and extracted with 4×50 ml ethyl acetate. The organics are combined, dried over magnesium sulfate, and concentrated to an orange solid residue.

The residue is chromatographed over 90 g silica gel (230–400 mesh), eluting with 3% ethyl acetate/hexane and collecting 20 ml fractions. Fractions 6–13 are combined and concentrated to afford 1.4 g of the title compound.

Mass spectrum: M/$_z$ (Relative Intensity); $[M+H]^+ = 307(7)$ $[M-PhCO_2]^+ = 185(100)$.

EXAMPLE 52

1-Chloro-3R-hydroxy-undec-1,5Z-diene

3R-Benzoyloxy-1-chloro-undec-1,5Z-diene (1.3 g, 4.24 mmole) is dissolved in 26 ml 1% sodium hydroxide-methanol and stirred at room temperature for 80 minutes in a 100 ml one-neck round bottom flask under nitrogen. The methanol is removed in vacuo and the residue taken up in 20 ml ethyl acetate. The organics are washed with 1×20 ml saturated sodium chloride and the aqueous layer is backwashed with 2×20 ml ethyl acetate. The combined organics are dried over magnesium sulfate and concentrated in vacuo to a pale oil.

The oil is chromatographed over 40 g silica gel (230–400 mesh), eluting with 10% ethyl acetate/hexane and collecting 12 ml fractions. Fractions 8–15 are combined and concentrated to provide 676 mg of the title compound.

Mass spectrum: M/$_z$ (Relative Intensity); $[M-H_2O]^- = 184(26)$.

EXAMPLE 53

3R-Hydroxy-undec-5Z-ene-1-yne

A flame dried 250 ml 3-neck round bottom flask under nitrogen is charged with 30 ml dry tetrahydrofuran and diisopropylamine (2.32 ml, 16.7 mmole) at 0° C. The solution is treated with n-butyllithium (8.61 ml, 13.3 mmole) slowly dropwise and allowed to stir 15 minutes at 0° C. 1-Chloro-3R-hydroxy-undec-1,5Z-diene (676 mg, 3.33 mole) in 3×1 ml dry tetrahydrofuran is added slowly dropwise to the reaction mixture at 0° C. The mixture is stirred one hour at 0° C., quenched with 2 ml saturated sodium chloride and poured into 20 ml saturated sodium chloride. The mixture is extracted with 4×20 ml ethyl acetate. The combined organics are dried over magnesium sulfate and concentrated in vacuo to a yellow oil.

The oil is chromatographed over 40 g silica gel (230–400 mesh), eluting with 10% ethyl acetate/hexane and collecting 12 ml fractions. Fractions 10–19 are combined and concentrated to afford 486 mg of the title compound.

Optical rotation: $[\alpha]_D^{23} = +14.0°$; (Hexane, c=6.6). Mass spectrum: M/$_z$ (Relative Intensity); $[M-C_7H_{13}]^+ = 69(83)$; $[M-C_4H_6O_1] = 96(26)$.

EXAMPLE 54

6-{6-[3(R)-Hydroxy-undec-5Z-ene-1-ynyl]-pyridine-2-yl}-5Z-hexenoic acid

3R-Hydroxy-undec-5Z-ene-1-yne (354 mg, 2.13 mmole) and pyridyl 6-[6-bromopyridinyl]-5Z-hexenoic acid (540 mg, 2 mmole) are combined in 5 ml degassed triethylamine in a 25 ml one-neck round bottom flask under argon. The solution is treated with (bis)triphenylphosphinepalladium dichloride (56 mg, 0.08 mmole), warmed to 55° C., and treated with cuprous ioxide (8 mg, 0.04 mmole). The reaction mixture is stirred 4 hours at 55° C., cooled to toom temperature, and the volatiles are removed in vacuo. The residue is taken up in 25 ml saturated ammonium chloride and the pH adjusted to 4.75 with 0.25N sodium hydrogen sulfate (pH meter). The mixture is extracted with 4×20 ml diethyl ether. The organics are combined, dried over magnesium sulfate, and concentrated in vacuo to a brown oil.

The oil is chromatographed over 24 g silica gel (230–400 mesh), eluting with 3% methanol/dichloromethane and collecting 4 ml fractions. Fractions 21–53 are combined and concentrated to provide 257 mg of the title compound.

TLC (silica gel-60, F-254); $R_f = 0.33$; (10% methanol/dichloromethane).

EXAMPLE 55

1,5-Unundecadien-3-ol, 1-[6-(6-hydroxy-1-hexenyl)-2-pyridinyl]-, [R-(E,Z,Z)]-

Sodium (bis)-2-methoxyethoxy-aluminum hydride (1.1 ml, 3.74 mmole) is dissolved in 8 ml dry toluene in an oven dried 50 ml 2-neck round bottom flask under nitrogen at 0° C. 6-{6-[3(R)-Hydroxy-undec-5Z-ene-1-ynyl]-pyridine-2-yl}-5Z-hexenoic acid (257 mg, 0.723 mmole), in 3×1 ml dry toluene, is added slowly dropwise to the reaction mixture at 0° C. The reaction mixture is stirred 4 hours at 0° C., quenched with 250 µl water, and stirred vigorously with 20 ml 0.5M sodium potassium tartrate and 20 ml ethyl acetate overnight. The aqueous phase is diluted with 25 ml saturated sodium chloride and extracted with 4×25 ml ethyl acetate. The organics are combined, dried over magnesium sulfate, and concentrated in vacuo to a pale oil.

The oil is chromatographed over 15 g silica gel (230–400 mesh) eluting with 45% ethyl acetate/hexane and collecting 3 ml fractions. Fractions 20–33 are combined and concentrated to give 142 mg of the title compound.

TLC (silica gel-60, F-254): R=0.51; (50% acetone/hexane). Mass spectrum: Calculated for $C_{22}H_{33}NO_2$: 343.2511; found: 343.2512.

EXAMPLE 56

6-{6-[3(S)-Hydroxy-undec-5Z-ene-1ynyl]-pyridine-2-yl}-5Z-hexen-1-ol

3S-Hydroxy-undec-5Z-ene-1-yne (72 mg, 0.281 mmole) and 6-[6-bromo-pyridine-2-yl]-5Z-hexen-1-ol (46 mg, 0.276 mmole) are combined in 2 ml degassed triethylamine in a 25 ml one-neck round bottom flask under argon. The solution is treated with (bis)triphenylphosphine palladium dichloride (4 mg, 0.006 mmole), warmed to 55° C., and treated with cuprous iodide (1 mg, 0.005 mmole). The reaction mixture is stirred 4 hours at 55° C., cooled to room temperature, and the volatiles removed in vacuo. The residue is partitioned between 1×15 ml 90% saturated sodium chloride/ammonium chloride 1:1 and 1×15 ml diethyl ether. The aqueous layer is further extracted with 3×10 ml diethyl ether. The organics are combined, dried over magnesium sulfate, and concentrated in vacuo to a dark yellow oil.

The oil is chromatographed over 7.2 g silica gel (230–400 mesh) eluting with 50% ethyl acetate/hexane and collecting 3 ml fractions. Fractions 15–24 are combined and concentrated to afford 53 mg of the title compound.

TLC (silica gel-60, F-254): $R_F$=0.34; (60% ethyl acetate/hexane).

EXAMPLE 57

1,5-Undecadien-3-ol, 1-[6-(6-hydroxy-1-hexenyl)-2-pyridinyl]-, [S-(E,Z,Z)]-

Sodium (bis)-2-methoxyethoxy-aluminum hydride (140 µl, 0.468 mmole) is dissolved in 1.5 ml dry toluene in an oven dried 25 ml 2-neck round bottom flask under nitrogen at 0° C. 6-{6-[3(S)-Hydroxy-undec-5Z-ene-1-ynyl]-pyridine-2-yl}-5Z-hexen-1-ol (50 mg, 0.146 mmole), in 3×0.5 ml dry toluene, is added slowly dropwise to the reaction mixture at 0° C. The reaction is stirred 2 hours at 0° C., quenched slowly with 100 µl water, and stirred vigorously with 1×10 ml 0.5M sodium potassium tartrate and 1×10 ml diethyl ether for one hour. The mixture is poured into 1×10 ml saturated sodium chloride and extracted with 4×10 ml diethyl ether. The organics are combined, dried over magnesium sulfate, and concentrated in vacuo to a yellow oil (55 mg).

The oil is chromatographed over 7.2 g silica gel (230–400 mesh), eluting with 45% ethyl acetate/hexane and collecting 4 ml fractions. Fractions 10–15 are combined and concentrated to give 45 mg of the title compound.

Optical rotation: $[\alpha]_D$= +3.4°; (Chloroform, c=4.5). Mass spectrum: Calculated for $_{22}H_{33}NO_2$: 343.2511; found: 343.2530.

EXAMPLE 58

Methyl-5-hydroxy-6-[5-(3-Hydroxy-undec-1E,5Z-dien-1yl)-phenyl-2-yl]-6-[2-carbomethoxy-ethylthio]-hexanoate Methyl-5,6-epoxy-6-[5-(3-hydroxy-undec-1E,5Z-dien-1yl)-phenyl-2yl]-hexanoate (18 mg, 0.0466 mmole) and methyl-3-mercapto-propionte (32 µl, 0.180 mmole) are combined in 1 ml methanol in a 10 ml one-neck round bottom flask under nitrogen. The solution is treated with triethylamine (52 µl, 0.373 mmole) and refluxed overnight. The reaction mixture is concentrated in vacuo and pumped under high vacuum for 2 hours.

The residue was chromatographed over 1 g silica sel (230–400 mesh), eluting with 30% ethyl acetate/hexane, and collecting 0.5 ml fractions. Fractions 21–45 are combined and concentrated to afford 13 mg of the title compound.

TLC (silica gel-60, F-254): $R_f$=0.06; (30% ethyl acetate/hexane).

EXAMPLE 59

Benzenehexanoic acid, ε-[(2-carboxyethyl)thio]-delta-hydroxy-3-(3-hydroxy-1,5-undecadienyl)-

Methyl-5-hydroxy-6-[5-(3-hydroxy-undec-1E,5Z-dien-1yl)-phenyl-2yl]-6-[2-carbomethoxy-ethylthiol]-hexanoate (12 ml, 0.024 mmole) is dissolved in 3 ml methanol in a 10 ml one-neck round bottom flask. The solution is treated with 0.5N sodium hydroxide (1 ml, 0.5 mmol) and stirred 4 hours at room temperature. The methanol is removed in vacuo and the aqueous residue diluted with 4 ml saturated sodium chloride. The pH of the mixture is adjusted to 3.2 with 0.25M sodium hydrogen sulfate (pH meter) and the mixture extracted with 3×10 ml diethyl ether. The organics are combined, dried over magnesium sulfate, and concentrated in vacuo to provide 8 mg of the title compound.

TLC (silica gel-60, F-254): $R_f$=0.22; (22% methanol/dichloromethane).

EXAMPLE 60

5-Hydroxy-6-[5-(3-hydroxy-undec-1E,5Z-dien-1yl)-phenyl-2yl]-6-[2-carbomethoxy-ethylthio]-hexane-1-ol 5,6-Epoxy-6-[5-(3-hydroxy-undec-1E,5Z-dienyl)-phenyl-hexan-1-ol (50 mg, 0.139 mmole) is dissolved in 2 ml methanol in a 10 ml one-neck round bottom flask under nitrogen. The solution is treated successively dropwise with triethylamine (78 ml, 0.559 mmole) and methyl-3-mercaptopropionate (62 ml, 0.559 mmole) and heated to reflux for 2 hours. The reaction mixture is concentrated in vacuo and pumped under high vacuum to remove excess mercaptopropionate.

The residue (81 mg) is chromatographed over 3.5 silica gel (230–400 mesh), eluting with 35% acetone/hexane and collecting 2 ml fractions. Fractions 11–21 are combined and concentrated to afford 51 mg of the title compound.

TLC (silica gel-60, F-254): $R_f$=0.32; (50% acetone/hexane).

EXAMPLE 61

Propanoic acid,
3-[[2,6-dihydroxy-1-[3-(3-hydroxy-1,5-undecadienyl)-phenyl]hexyl]thio]-

5-Hydroxy-6-[5-(3-hydroxy-undec-1E,5Z-dien-1yl)-phenyl-2yl]-6-[2-carbomethoxy-ethylthio]-hexane-1-ol (33 mg, 0.069 mmole) is dissolved in 2 ml methanol in a 25 ml one-neck round bottom flask. The solution is treated with 0.5N sodium hydroxide (1 ml, 0.5 mmole). The reaction mixture is stirred for one hour at room temperature, the methanol removed in vacuo, and the pH of the aqueous residue adjusted to 3.0 with 0.25M sodium hydrogen sulfate (pH meter). The mixture is extracted with 4×10 ml diethyl ether. The organics are combined, dried over magnesium sulfate, and concentrated in vacuo to afford 28 mg of the title compound.

TLC (silica gel-60, F-254): $R_f = 0.11$; (50% acetone/hexane).

EXAMPLE 62

Methyl-N-[N-trifluoroacetyl-S-[1-[5-(3-hydroxy-undec-1E,5Z-dien-1yl)-phenyl-2yl]-1-[4-carbmethoxy-1-hydroxy-butyl]-methyl]-L-cysteinyl]glycinate Methyl-5,6-epoxy-6-[5-(3-hydroxy-undec-1E,5Z-dien-1yl)-phenyl-2yl]-hexanoate (50 mg, 0.129 mole) and methyl-N-trifluoro-acetyl-L-cysteinylglycinate (130 mg, 0.452 mmole) are combined in 2 ml dry methanol in a 10 ml one-neck round bottom flask under argon. The solution is treated with triethylamine (116 µl, 0.834 mmole) and refluxed for 4.5 hours. The reaction mixture is concentrated in vacuo to a pale residue.

The residue is chromatographed over 3.5 g silica gel (230-400 mesh), eluting with 27% acetone/hexane and collecting 1.5 ml fractions. Fractions 19-38 are combined and concentrated to afford 74 mg of the title compound.

TLC (silica gel-60, F-254): $R_f = 0.42$; (50% acetone/hexane).

EXAMPLE 63

Glycine,
N-[S-[5-carboxy-2-hydroxy-1-[3-(3-hydroxy-1,5-undecadienyl)phenyl)pentyl]-L-cysteinyl]-, disodium salt Methyl-N-[N-trifluoroacetyl-S-[1-[5-(3-hydroxy-undec-1E,5Z-dien-1yl)-phenyl-2yl]-1-[4-carbmethoxy-1-hydroxy-butyl]-methyl]-L-cysteinyl]glycinate (36 mg, 0.0534 mmole) is dissolved in 1 ml methanol in a 25 ml one-neck round bottom flask under nitrogen. The solution is treated with 0.11N sodium hydroxide (1.48 ml, 0.163 mmole) and stirred 24 hours at room temperature. The methanol is removed in vacuo and the aqueous residue is lyophilized to provide 40 mg of the title compound contaminated with sodium trifluoroacetate.

TLC (MKC$_{18}$-RP-TLC): $R_f = 0.72$; (70% methanol/water, acetic acid 0.1%, buffered to pH=5.0 with 2M ammonium hydroxide).

EXAMPLE 64

Glycine,
N-[S-[2,6-dihydroxy-1-[3-(3-hydroxy-1,5-undecadienyl)phenyl]hexyl]-N-(trifluoroacetyl)-L-cysteinyl]-, methyl ester 5,6-Epoxy-6-[5-(3-hydroxy-1E,5Z-undecadienyl)-phenyl]-hexan-1-ol (60 mg, 0.167 mmole) is dissolved in 2 ml dry methanol in a 10 ml one-neck round bottom flask under argon. The reaction mixture is treated successively with triethylamine (150 ml, 1.08 mmole) and methyl-N-trifluoroacetyl-L-cysteinyl-glycinate (150 mg, 0.520 mmole) and heated to reflux for 4 hours. The mixture is cooled to room temperature and concentrated in vacuo to a pale oil.

The oil is chromatographed over 5 g silica gel (230-400 mesh), eluting with 40% acetone/hexane and collecting 1.5 ml fractions. Fractions 18-40 are combined and concentrated to afford 88 mg of the title compound.

TLC (silica gel-60, F-254): $R_f = 0.26$; (50% acetone/hexane). Mass spectrum: M/Z (relative intensity); (M-H$20)^+ = 629$ (3); $[M-2H$20]^+ = 611$ (2); [M-C$8S1SOFS3NS20S4S-2HS20=H[+=323 (81); [M-C$8HS1S5-HS20+H]^+ = 519$ (7).

EXAMPLE 65

Glycine,
N-[S-[2,6-dihydroxy-1-[3-(3-hydroxy-1,5-undecadienyl)phenyl]hexyl]-L-cysteinyl]-

Methyl-N-[N-trifluoroacetyl-S-[1,4-dihydroxy-butyl-1-[5-(3-hydroxy-undec-1E,5Z-dien-1yl)-phenyl-2yl]-methyl-L-cysteinyl]-glycinate (15 mg, 0.024 mmole) is dissolved in 2 ml methanol in a 10 ml one-neck round bottom flask under nitrogen. The solution is treated with 1.0M sodium carbonate (1.0 ml, 1.0 mmole) and stirred at room temperature for 4 hours. The reaction is diluted with 1 ml water and the pH adjusted to 5.5 with 10% acetic acid/water (pH meter). The methanol is blown off under a stream of nitrogen and the aqueous residue concentrated to dryness.

The residue is dissolved in 1 ml high purity water and chromatographed over a 10×25 cm C-18 RP-HPLC column in 10 equal injections. (Methanol/water/acetic acid; 70:30:1.0, buffered to pH=5.6 with 2.0M ammonium hydroxide; 3 ml min, 245 nm). Two fractions are collected and each is concentrated in vacuo to afford 6.5 mg each of two diasteromeric mixtures of the title compound.

EXAMPLE 66

6-[1-[6-(3-Hydroxy-propyn-1-yl)-pyridine-2yl]-methyl]-pyran-2-one

6 Bromo pyridine-2yl]-methylpyran-2-one (57 mg, 0.211 mmole) and propargyl alcohol (18 µl, 0.309 mmole) are combined in 1 ml degassed triethylamine in a 10 ml one-neck round bottom flask under argon. The mixture is treated with (bis)triphenylphosphine palladium dichloride (8 mg, 0.011 mmole), warmed to 55° C., and is treated with cuprous iodide (2 mg, 0.011 mmole). The reaction mixture is stirred at 55° C. for 2 hours, cooled to room temperature, and the volatiles are removed in vacuo. The residue is taken up in 1×10 ml ethyl acetate and washed with 1×10 ml 90% saturated 1:1 sodium chloride/ammonium chloride. The aqueous layer is backwashed with 3×10 ml ethyl acetate. The combined organics are dried over magnesium sulfate and concentrated in vacuo to a yellow oil.

The oil is chromatographed over 5.7 g silica gel (230-400 mesh), eluting with 45% acetone/hexane and collecting 2 ml fractions. Fractions 21-30 are combined and concentrated to afford 25 mg of the title compound.

TLC (silica gel-60, F-254): $R_f = 0.19$; (50% acetone/hexane).

EXAMPLE 67

(a)
6-[6-(3-Hydroxy-1-propenyl)-2-pyridinyl]-1,5-hexanediol (b)
Hexahydro-6-[[6-(3-hydroxy-1-propenyl)-2-pyridinyl]-methyl]-2H-pyran-2-ol Sodium (bis) 2-methoxyethoxy aluminum hydride (0.15 ml, 0.510 mmole) is dissolved in 1 ml dry toluene in an oven-dried 10 ml 2-neck round bottom flask under argon at 0° C. 6-[1-[6-(3-Hydroxy-propyn-1-yl)-pyridine-2yl]-methyl]pyran-2-one (25 mg, 0.102 mmole), in 3×0.3 ml dry toluene, is added dropwise to the reaction mixture. The mixture is stirred 30 minutes at 0° C. and at room temperature overnight. The reaction is quenched with 5 ml 0.5M sodium potassium tartrate, diluted with 5 ml dichloromethane, and is stirred vigorously for 2 hours. The mixture is poured into 15 ml saturated sodium chloride and extracted with 4×10 ml ethyl acetate. The combined organics are dried over magnesium sulfate and concentrated in vacuo to a yellow oil (22 mg).

The oil is chromatographed over 3.5 g silica gel (230–400 mesh), eluting with 65% acetone/hexane and collecting 1.5 ml fractions. Fractions 5–10 are combined and concentrated to afford 5 mg (20%) of title compound (a). Fractions 13–21 are combined and concentrated to provide 12 mg (47%) of title compound (b).

(a) Mass spectrum: Calculated for $C_{14}H_{21}NO_3$: 251.1521; found: 251.1510.

(b) Mass spectrum: Calculated for $C_{14}H_{19}NO_3$: 249.1365; found: 249.1359.

EXAMPLE 68

Methyl-5,6-epoxy-6-[6-(3-hydroxy-propyl-1yl)pyridine-2yl]-hexanoate

Propargyl alcohol (25 μl, 0.433 mmole) and methyl-5,6-epoxy-6-[6-bromopyridine-2yl]-hexanoate (100 mg, 0.333 mmole) are combined in 1 ml triethylamine in a 10 ml one-neck round bottom flask under argon. The solution is treated with (bis)triphenylphosphine palladium dichloride (21 mg, 0.030 mmole), warmed to 55° C., and treated with cuprous iodide (3 mg, 0.015 mmole). The reaction mixture is cooled to room temperature and diluted with 5 ml dichloromethane. The mixture is poured into 15 ml 90% saturated sodium chloride and is extracted with 4×10 ml ethyl acetate. The combined organics are dried over magnesium sulfate and concentrated in vacuo to an amber oil.

The oil is chromatographed over 10.7 g silica gel (230–400 mesh), eluting with 40% acetone/hexane and collecting 3 ml fractions. Fractions 18–26 are combined and concentrated to provide 72 mg of the title compound.

TLC (silica gel-60, F-254): $R_f=0.33$; (50% acetone/hexane).

EXAMPLE 69

3-[6-(3-Hydroxy-1-propenyl)-2-pyridinyl]-oxiranebutanol

Sodium (bis) 2-methoxyethoxy-aluminum hydride (0.31 ml, 1.05 mmole) is dissolved in 1 ml toluene in an oven-dried 10 ml 2-neck round bottom flask under nitrogen at 0° C. Methyl-5,6-epoxy-6-[6-(3-hydroxy-propyl-1yl)pyridine-2yl]-hexanoate (72 mg, 0.263 mmole), in 3×0.3 ml toluene, is added dropwise to the reaction mixture at 0° C. The reaction mixture is stirred 4 hours at 0° C., quenched with the careful addition of 5 ml 0.5M sodium potassium tartrate, and stirred vigorously for 1.5 hours while warming to room temperature. The mixture is poured into 15 ml saturated sodium chloride and extracted with r×10 ml ethyl acetate. The combined organics are dried over magnesium sulfate and concentrated in vacuo to an amber oil (64 mg).

The oil is chromatographed over 6 g silica gel (230–400 mesh), eluting with 50% acetone/hexane and collecting 2 ml fractions. Fractions 22–39 are combined and concentrated to afford 45 mg of the title compound.

Mass spectrum: Calculated for $C_{14}H_{19}NO_3$: 249.1365; found: 249.1356.

EXAMPLE 70

6-[6-Bromo-pyridine-2yl]-5,6-epoxy-hexane-1-ol

6-[6-Bromo-pyridine-2yl]-5-hexen-1-ol (68 mg, 0.265 mmole) is dissolved in 2 ml dry dichloromethane in an oven dried 5 ml 2-neck round bottom flask under nitrogen. The mixture is cooled to 0° C. and treated with m-chloroperbenzoic acid (59 mg, 0.292 mmole). The reaction mixture is stirred 3 hours at 0° C., warmed to room temperature, and stirred an additional 3 hours. The reaction is quenched with 2 ml saturated sodium sulfite and poured into 10 ml saturated sodium bicarbonate. The mixture was extracted with 3×10 ml diethyl ether. The combined organics are dried over magnesium sulfate and concentrated in vacuo to a colorless oil (70 mg).

The oil is chromatographed over 5 g silica gel (230–400 mesh), eluting with 45% ethyl acetate/hexane and collecting 2 ml fractions. Fractions 14–24 are combined and concentrated to afford 44 mg of the title compound.

TLC (silica gel-60, F-254): $R_f=0.24$; (60% ethyl acetate/hexane).

EXAMPLE 71

6-[1-[6-(3-Hydroxy-undec-1ynyl)-pyridine-2yl]-methyl]-pyran-2-one

3-Hydroxy-undec-1-yne (202 mg, 1.2 mmole) and 6-[1-[6-bromopyridine-2yl]methyl]pyran-2-one (270 mg, 1 mmole) are combined in 4 ml triethylamine in a 25 ml one-neck round bottom flask under argon. The mixture is treated with (bis)triphenylphosphine palladium dichloride (14 mg, 0.02 mmole), warmed to 55° C., and is treated with cuprous iodide (2 mg, 0.01 mmole). The reaction mixture is stirred one hour at 55° C., cooled to room temperature, and the volatiles are removed in vacuo. The residue is partitioned between 1×10 ml diethyl ether and 1×10 ml saturated sodium chloride/ammonium chloride (1:1). The aqueous layer is extracted with 3×10 ml diethyl ether. The combined organics are dried over magnesium sulfate and concentrated in vacuo to a brown oil.

The oil is chromatographed over 15 g silica gel (230–400 mesh), eluting with 65% ethyl acetate/hexane and collecting 5 ml fractions. Fractions 18–45 are combined and concentrated to give 320 mg of the title compound.

Mass spectrum: M/z (Relative Intensity); [M+[=357(5); [M-$C_8H_{17}$]+ =244(100).

EXAMPLE 72

3-[6-(3-Hydroxy-1-undecynyl)-2-pyridinyl]-oxiranebutanol

3-Hydroxy-undec-1-yne (33 mg, 0.194 mmole) and 5,6-epoxy-6[6-bromopyridine-2yl]hexane-1-ol (44 mg, 0.162 mmole) are combined in 1 ml degassed triethylamine in a 25 ml one-neck round bottom flask under argon. The solution is treated with (bis)triphenylphosphine palladium dichloride (3 mg, 0.004 mmole), warmed to 55° C., and is treated with cuprous iodide (1 mg, 0.005 mmole). The reaction mixture is stirred 1.5 hours at 55° C., cooled to room temperature, and the volatiles are removed in vacuo. The residue is partitioned between 1×10 ml diethyl ether and 1×10 ml saturated sodium chloride/ammonium chloride (1:1). The aqueous layer is further extracted with 3×10 ml diethyl ether. The combined organics are dried over magnesium sulfate and concentrated in vacuo to a pale oil.

Mass spectrum: Calculated for $C_{22}H_{33}NO_3$: 359.2460; found: 359.2472.

EXAMPLE 73

1-[6-(6-Hydroxy-1-hexenyl)-2-pyridinyl]-1-undecyn-3-ol (Z)-

3-Hydroxy undec-1-yne (65 mg, 0.388 mmole) and 6-[6-bromopyridine-2yl]-5Z-hexene-1-ol (83 mg, 0.324 mmole) are combined in 2 ml degassed triethylamine in a 25 ml one-neck round bottom flask under argon. The solution is treated with (bis)triphenylphosphine palladium dichloride (7 mg, 0.01 mmole), warmed to 55° C., and treated with cuprous iodide (1 mg, 0.05 mmole). The reaction mixture is stirred 1.5 hours at 55° C., cooled to room temperature, and the volatiles are removed in vacuo. The residue is partitioned between 1×10 ml diethyl ether and 1×10 ml saturated sodium chloride/ammonium chloride (1:1). The aqueous layer is extracted with 3×10 ml diethyl ether. The combined organics are dried over magnesium sulfate and concentrated in vacuo to a pale oil.

The oil is chromatographed over 6.5 g silica gel (230-400 mesh), eluting with 55% ethyl acetate/hexane and collecting 3 ml fractions. Fractions 10-17 are combined and concentrated to afford 101 mg of the title compound.

Mass spectrum: Calculated for $C_{22}N_{33}NO_2$: 343.2511; found: 343.2499.

EXAMPLE 74

6-[6-(3-Hydroxy-5-undecenyl)-2-pyridinyl]-1,5-hexanediol

Sodium (bis) 2-methoxyethoxy-aluminum hydride (0.52 ml, 1.78 mmole) is dissolved in 2 ml dry toluene in an oven-dried 50 ml 2-neck round bottom flask under nitrogen at 0° C. 6-[1-[6-(3-Hydroxy-undec-1ynyl)-pyridine-2yl]-methyl-]pyran-2-one (160 mg, 0.445 mmole), in 2×1 ml dry toluene, is added slowly dropwise to the reaction mixture at 0° C. The mixture is stirred 7 hours at 0° C., quenched with 0.100 ml water, and stirred vigorously overnight with 10 ml 0.5M sodium potassium tartrate. The mixture is extracted with 4×10 ml ethyl acetate. The combined organics are dried over magnesium sulfate and concentrated in vacuo to a pale oil.

The oil is chromatographed over 9 g silica gel (230-400 mesh), eluting with ethyl acetate and collecting 3 ml fractions. Fractions 20-45 are combined and concentrated to provide 126 mg of the title compound.

Mass spectrum: Calculated for $C_{22}H_{37}NO_3$: 363.2773; found: 363.2786.

EXAMPLE 75

1-[6-(6-hydroxy-1-hexenyl)-2-pyridinyl]-1-undecen-3-ol (E,Z)-

Sodium (bis) 2-methoxyethoxy-aluminum hydride (0.24 ml, 0.816 mmole) is dissolved in 3 ml dry toluene in an oven-dried 50 ml 2-neck round bottom flask under nitrogen at 0° C. 6-[6-(3-Hydroxy-undeclynyl)-pyridine-2yl]-5Z-hexene-1-ol (89 mg, 0.259 mmole), in 3×1 ml dry toluene, is added slowly dropwise to the reaction mixture at 0° C. The reaction mixture is stirred 2 hours at 0° C., quenched with 0.100 ml water, and is stirred vigorously with 1×10 ml saturated sodium chloride and extracted with 4×10 ml ethyl acetate. The combined organics are dried over magnesium sulfate and concentrated in vacuo to a pale yellow oil.

The oil is chromatographed over 6.5 g silica gel (230-400 mesh), eluting with 45% ethyl acetate/hexane and collecting 3 ml fractions. Fractions 14-22 are combined and concentrated to give 67 mg (75%) of the title compound.

Mass spectrum: Calculated for $C_{22}H_{35}NO_2$: 345.2668; found: 345.2663.

EXAMPLE 76

3-[6-(3-Hydroxy-1-undecenyl)-2-pyridinyl]-oxiranebutanol

Sodium (bis) 2-methoxyethoxy-aluminum hydride (0.10 ml, 0.340) is dissolved in 2 ml dry toluene in an oven-dried 25 ml 2-neck round bottom flask under nitrogen at 0° C. 5,6-Epoxy-6-[6-(3-hydroxy-undeclynyl)-pyridine-2yl]hexane-1-ol (32 mg, 0.089 mmole), in 2×1 ml dry toluene, is added slowly dropwise to the reaction mixture at 0° C. The reaction mixture is stirred 2 hours at 0° C., quenched with 0.100 ml water, and stirred vigorously with 1×10 ml 0.5M sodium potassium tartrate for one hour. The mixture is poured into 1×10 ml sodium chloride and extracted with 4×10 ml ethyl acetate. The combined organics are dried over magnesium sulfate and concentrated in vacuo to a pale oil.

The oil is chromatographed over 5 g silica gel (230-400 mesh), eluting with 85% ethyl acetate/hexane and collecting 3 ml fractions. Fractions 34-48 are combined and concentrated to provide 23 mg of the title compound.

Mass spectrum: Calculated for $C_{22}H_{35}NO_3$: 361.2617; found: 361.2602.

EXAMPLE 77

6-[6-(3-Hydroxy-5-undecenyl)-2-pyridinyl]-1,5-hexanediol

Sodium (bis) 2-methoxyethoxy-aluminum hydride (24 ml, 82 mmol) is dissolved in 150 ml dry toluene in a flame-dried, 500 ml 3-neck round bottom flask under nitrogen at 0° C. 6-[1-[6-(3-hydroxyl-5-undecen-1-ynyl)-pyridinyl]methyl]pyran-2-one (5.83 g, 14 mmole), in 4×10 ml dry toluene, is added slowly dropwise to the reaction mixture at 0° C. The reaction is stirred 20 minutes at 0° C. and then an additional 7 hours at room temperature. The reaction is quenched by the careful addition of 3 ml water. The mixture is stirred vigorously overnight with 1×160 ml 0.5M sodium potassium tartrate. The mixture is extracted with 3×100 ml ethyl acetate. The combined organics are washed with 1×100 ml saturated sodium chloride and dried over magnesium sulfate. The organics are concentrated in vacuo to a crude amber oil (35 g).

The oil is chromatographed over 180 g silica gel (230-400 mesh), eluting with ethyl acetate, and collecting 50 ml fractions for 47 fractions when elution is continued with 10% acetone/ethyl acetate. Fractions 9-30 are combined and concentrated to provide 3.23 g (55%) of 10,11-allylic alcohol as a yellow solid. Fractions 40-63 are combined and concentrated to afford 1.0 g of the title compound.

Mass spectrum: Calculated for $C_{22}H_{37}NO_3$: 363.2773; found: 363.2763.

EXAMPLE 78

1-[6-Bromo-pyridine-2-yl]-1-hexyne 2,6-Dibromopyridine (2.36 g, 10 mmole) is suspended in 32 ml degassed triethylamine in a 100 ml one-neck round bottom flask under argon. The suspension is treated successively with (bis)triphenylphosphine palladium dichloride (62 mg, 0.08 mmole) and cuprous iodide (8 mg, 0.04 mmole) and is warmed to 50° C. 1-Hexyne (0.50 ml, 4.4 mmoles), in 4 ml triethylamine, is added slowly dropwise to the reaction mixture over 30 minutes at 50° C. The reaction is stirred an additional one hour at 50° C., cooled to room temperature, and the triethylamine hydrobromide is removed by filtration. The filtrate is concentrated in vacuo to a white pasty solid.

The solid is chromatographed over 50 g silica gel (239-400 mesh), eluting with 8% ethyl acetate/hexane and collecting 5 ml fractions. Fractions 9-16 are combined and concentrated to afford 520 mg of pyridyl bromide and (bis) alkylated contaminant as a colorless oil. The oil is chromatographed over 25 g silica gel (230-400 mesh), eluting with 40% dichloromethane/hexane, and collecting 5 ml fractions. Fractions 16-27 are combined and concentrated to afford 439 mg of the title compound.

Mass spectrum: Calculated for $C_{11}H_{12}BrN$: 237.0154; found: 237.0143.

EXAMPLE 79

1-[6-Bromopyridine-2yl]-1Z-hexene

1-[6-Bromo-pyridine-2yl]-1-hexyne (300 mg, 1.26 mmole) is dissolved in 7 ml hexane in a 25 ml one-neck round bottom flask. The solution is treated successively with glacial acetic acid (89 μl, 1.48 mmole) and 5% palladium on barium sulfate (35 mg). The reaction mixture is hydrogenated at atmospheric pressure until 28 ml of hydrogen is taken up. The mixture is filtered through celite and the filter cake washed well with acetone. The filtrate is concentrated in vacuo to a pale yellow oil.

The oil is chromatographed over 35 g silica gel (230-400 mesh), eluting with 20% dichloromethane/hexane and collecting 9 ml fractions. Fractions 19-43 are combined and concentrated to provide 180 mg of the title compound.

TLC (silica gel-60, F-254): $R_f=0.15$; (20% dichloromethane/hexane).

EXAMPLE 80

1-[6-Bromopyridine-2yl]-1,2-epoxy-hexane

1-[6-Bromopyridine-2yl]-1Z-hexene (74 mg, 0.310 mmole) is dissolved in 3 ml dichloromethane in a 25 ml one-neck round bottom flask under nitrogen. The solution is cooled to 0° C. and treated with m-chloroperbenzoic acid. The mixture is stirred at 0° C., warmed to room temperature, and stirred and additional 6 hours. The reaction is quenched with 2 ml saturated sodium sulfite and diluted with 10 ml diethyl ether. The organics are washed successively with 1×10 ml saturated sodium bicarbonate and 1×10 ml saturated sodium chloride. The organics are dried over magnesium sulfate and concentrated in vacuo to a colorless oil (65 mg).

The oil is chromatographed over 5 g silica gel (230-400 mesh), eluting with 10% ethyl acetate/hexane and collecting 3 ml fractions. Fractions 5-8 were combined and concentrated to afford 56 mg of the title compound.

TLC (silica gel-60, F-254): $R_f=0.58$;(30% ethyl acetate/hexane).

EXAMPLE 81

1-[6-(3-Hydroxy-undec-5Z-en-lynyl)-pyridine-2yl]-1-Z-hexene

3Hydroxy-undec-5Z-en-1-yne (62 mg, 0.370 mmole) and 1-[6-Bromopyridine-2yl]-1Z-hexene (74 mg, 0.370 mmole) are combined in 1 ml degassed triethylamine in a 10 ml one-neck round bottom flask under argon. The solution is treated with (bis)triphenylphosphine palladium dichloride (2 mg, 0.003 mmole), warmed to 75° C., and treated with cuprous iodide (1 mg, 0.005 mmole). The reaction is stirred at 75° C. for 2 hours, cooled to room temperature, and the volatiles removed in vacuo. The residue is partitioned between 1×10 ml 90% saturated sodium chloride/ammonium chloride (1:1) and 1×10 ml diethyl ether. The aqueous layer is extracted with 3×10 ml diethyl ether. The combined organics were dried over magnesium sulfate and concentrated in vacuo to a pale oil.

The oil is chromatographed over 7 g silica gel (230-400 mesh), eluting with 8% ethyl acetate/hexane and collecting 3 ml fractions. Fractions 29-48 are combined and concentrated to afford 85 mg of the title compound.

TLC (silica gel-60, F-254); $R_f=0.44$; (30% ethyl acetate/hexane).

EXAMPLE 82

1,2-Epoxy-1-[6-(3-hydroxy-undec-5Z-en-lynyl)-pyridine-2yl]-hexane

3-Hydroxy undec-5Z-en-1-yne (44 mg, 0.262 mmole) and 1-[6-Bromopyridine-2yl]-1,2-epoxy-hexane (56 mg, 0.219 mmole) are combined in 1 ml degassed triethylamine in a 10 ml one-neck round bottom flask under argon. The solution is treated with (bis)triphenylphosphine palladium dichloride (2 mg, 0.003 mmole), heated to 75° C., and treated with cuprous iodide (1mg, 0.005 mmole). The reaction mixture is stirred at 75° c. for 2 hours, cooled to room temperature, and the volatiles removed in vacuo. The residue is partitioned between 1×10 ml 90% saturated chloride/ammonium chloride (1:1) and 1×10 ml diethyl ether. The aqueous layer is extracted with 3×10 ml diethyl ether. The combined organics are dried over magnesium sulfate and concentrated in vacuo to a brown oil.

The oil is chromatographed over 6 g silica gel (230-400 mesh), eluting with 20% ethyl acetate/hexane and collecting 3 ml fractions. Fractions 17-30 are combined and concentrated to afford 48 mg of the title compound.

TLC (silica gel-60, F-254): $R_f = 0.18$; (30% ethyl acetate/hexane).

EXAMPLE 83

1-[6-(1-hexenyl)-2-pyridinyl]-1,5-undecadien-3-ol (E,Z,Z)-

Sodium (bis) 2-methoxyethoxy-aluminum hydride (0.154 ml, 0.522 mmole) is dissolved in 2 ml dry toluene in an oven-dried 25 ml 2-neck round bottom flask under nitrogen at 0° C. 1-[6-(3-Hydroxy-undec-5Z-en-lynyl)-pyridine-2-yl]-1-Z-hexene (85 mg, 0.261 mmole), in 3×0.5 ml dry toluene, is added slowly dropwise to the reaction mixture at 0° C. The reaction is stirred 2 hours at 0° C., quenched with 0.150 ml water, and stirred vigorously with 1×10 0.5M sodium potassium tartrate and 1×10 ml diethyl ether for one hour. The mixture is poured into 1×10 ml sodium chloride and extracted with 3×10 ml diethyl ether. The combined organics are dried over magnesium sulfate and concentrated in vacuo to a yellow oil.

The oil is chromatographed over 5 g silica gel (230–400 mesh), eluting with 15% ethyl acetate/hexane and collecting 3 ml fractions. Fractions 7–10 are combined and concentrated to provide 61 mg of the title compound.

Mass spectrum: Calculated for $C_{22}H_{33}NO$: 327.2562; found: 327.2552.

EXAMPLE 84

1-[6-(3-Butyloxiranyl)-2-pyridinyl]-1,5-undecadien-3-ol

Sodium (bis) 2-methoxyethoxy-aluminum hydride (0.124 ml, 0.422 mmole) is dissolved in 2 ml dry toluene in an oven-dried 25 ml 2-neck round bottom flask under nitrogen at 0° C. 1,2-Epoxy-1-[6-(3-hydroxy-undec-5Z-en-lynyl)-pyridine-2yl]-hexane (48 mg, 0.141 mmole), in 3×0.5 ml dry toluene, is added slowly dropwise to the reaction mixture at 0° C. The reaction is stirred 2 hours at 0° C., quenched with 0.150 ml water, and stirred vigorously with 1×10 ml 0.5M sodium potassium tartrate and 1×10 ml diethyl ether for one hour. The mixture is poured into 1×10 ml saturated sodium chloride and extracted with 3×10 ml diethyl ether. The combined organics are dried over magnesium sulfate and concentrated in vacuo to a pale oil.

The oil is chromatographed over 5.5 g silica gel (230–400 mesh), eluting with 20% ethyl acetate/hexane and collecting 3 ml fractions. Fractions 8–13 are combined and concentrated to afford 28 mg of the title compound.

Mass spectrum: Calculated for $C_{22}H_{33}NO_2$: 343.2511; found: 343.2495.

EXAMPLE 85

1-[5-(6-Hydroxy-1-hexenyl)-2-furanyl]-1,5-undecadien-3-ol (Z,E,Z)

1-t-Butyldimethylsilyloxy-6-[5-(3-hydroxy-undec-1E,5Z-dien-1-yl)-furan-2-yl]-5Z-hexene (230 mg, 0.515 mmole) is dissolved in 5 ml dry tetrahydrofuran in a 50 ml one-neck round bottom flask. The solution is treated dropwise with tetra-n-butylammonium fluoride (0.62 ml, 0.62 mmole) and stirred 3 hours at room temperature. The reaction mixture is diluted with 3 ml saturated sodium chloride/sodium bicarbonate (1:1) and the tetrahydrofuran is removed in vacuo. The residue is poured into 10 ml saturated sodium bicarbonate and extracted with 4×10 ml diethyl ether. The organics are combined, dried over magnesium sulfate, and are concentrated in vacuo to a yellow oil.

The oil is chromatographed over 9 g silica gel (230–400 mesh) eluting with 20% ethyl acetate/hexane and collecting 6 ml fractions. Fractions 12–22 are combined and concentrated to give 160 mg of the title compound.

TLC (silica gel-60, F-254): $R_f = 0.13$ (30% ethyl acetate/hexane).

EXAMPLE 86

1-[5-(6-Hydroxy-1-hexenyl)-2-furanyl]-5-undecen-1-yn-3-ol (Z,Z)

1t-Butyldimethylsilyloxy-6-[5-(3-hydroxy-undec-5Z-ene-1-ynyl)-furan-2-yl]-5Z-hexene (70 mg, 0.157 mmole) is dissolved in 2 ml dry tetrahydrofuran in an oven dried 10 ml 2-neck round bottom flask under nitrogen. The solution is cooled to 0° C. and treated with 1M tetra-n-butylammonium fluoride (0.19 ml, 0.19 mmole). The reaction mixture is stirred 30 minutes at 0° C., warmed to room temperature, and stirred 2 hours. The reaction is diluted with 1 ml saturated sodium bicarbonate and the tetrahydrofuran is removed in vacuo. The residue is poured into 10 ml saturated sodium bicarbonate and extracted with 4×10 ml diethyl ether. The organics are combined, dried over magnesium sulfate and concentrated in vacuo to a yellow oil.

The oil is chromatographed over 3 g silica gel (230–400 mesh) eluting with 20% ethyl acetate/hexane and collecting 2 ml fractions. Fractions 9–17 are combined and concentrated to afford 38 mg of the title compound.

TLC (silica gel-60, F-254): $R_f = 0.11$ (30% ethyl acetate/hexane).

EXAMPLE 87

6-[5-(3-Hydroxy-1,5-undecadienyl)-2-furanyl]-5-hexenoic acid, (E,E,Z)

Methyl-6-[5-(3-hydroxyundec-1E,5Z-dien-1-yl)furan-2-yl]-5E-hexenoate (2.0 mg, 0.0055 mmole) is dissolved in 750 µl methanol in a 10 ml one-neck round bottom flask under nitrogen. The solution is treated with 0.5N lithium hydroxide (0.25 ml, 0.125 mmole) and the reaction mixture is stirred at room temperature for 3 hours. The methanol is removed in vacuo and the pH of the aqueous residue is adjusted to 3.5 with 0.25M sodium hydrogen sulfate (pH meter). The mixture is poured into 10 ml saturated sodium chloride and extracted with 4×10 ml ethyl acetate. The organics are combined, dried over sodium sulfate and concentrated in vacuo to provide 1.8 mg of the title compound.

TLC (silica gel-60, F-254): $R_f = 0.39$ (50% acetone/hexane).

EXAMPLE 88

6-[5-(3-Hydroxy-1,5-undecadienyl-2-furanyl]-5-hexenoic acid (Z,E,Z)

Methyl-6-[5-(3-hydroxyundec-1E,5Z-dien-1-yl)furan-2-yl]-5E-hexenoate (1.7 mg, 0.0047 mmole) is dissolved in 750 µl methanol in a 10 ml one-neck round bottom flask under nitrogen. The solution is treated with 0.5N lithium hydroxide (0.25 ml, 0.125 mmole) and the reaction mixture is stirred at room temperature for 3 hours. The methanol is removed in vacuo and the pH of the aqueous residue is adjusted to 3.5 with 0.25M sodium hydrogen sulfate (pH meter). The mixture is poured into 10 ml saturated sodium chloride and extracted with 4×10 ml ethyl acetate. The organics are combined, dried over sodium sulfate, and concentrated in vacuo to afford 1.5 mg of the title compound.

TLC (silica gel-60, F-254): $R_f = 0.39$ (50% acetone/hexane).

EXAMPLE 89

6-[5-(3-Hydroxy-1,5-undecadienyl)-2-furanyl]-1,5-hexanediol

Sodium (bis) 2-methoxyethoxy-aluminum hydride (3.4M/toluene; 0.322 ml, 1.10 mmole) is dissolved in 1 ml dry toluene in an oven dried 10 ml 2-neck round bottom flask under nitrogen. The solution is cooled to $-22°$ C. and methyl-5-hydroxy-6-[5-(3-hydroxy-undec-5Z-ene-1-ynyl)-furan-2-yl]-hexanoate (75 mg, 0.199 mmole), in 3×0.5 ml dry toluene, is added slowly dropwise to the reaction mixture. The reaction is stirred 1 hour at $-22°$ C., warmed to 0° C., and stirred an additional hour. The reaction is quenched at 0° C. with 200 μl water, diluted with 5 ml diethyl ether, and stirred vigorously with 5 ml 0.5M sodium potassium tartrate for 1 hour. The mixture is poured into 10 ml saturated sodium chloride and extracted with 4×10 ml diethyl ether. The organics are combined, dried over magnesium sulfate, and concentrated in vacuo to a yellow oil.

The oil is chromatographed over 8 g silica gel (230-400 mesh), eluting with 30% acetone/hexane and collecting 3 ml fractions. Fractions 23-42 are combined and concentrated to provide 53 mg of the title compound.

TLC (silica gel-60, F-254): $R_f = 0.35$ (50% acetone/hexane).

EXAMPLE 90

δ-Hydroxy-5-(3-hydroxy-5-undecen-1-ynyl)-2-furanhexanoic acid

Methyl-5-hydroxy-6-[5-(3-hydroxy-undec-5Z-ene-1-ynyl)-furan-2-yl]-hexanoate (15 mg, 0.040 mmole) is dissolved in 1.6 ml methanol in a 10 ml one-neck round bottom flask under nitrogen. The solution is treated with 0.5N sodium hydroxide (0.8 ml, 0.40 mmole) and the reaction mixture is stirred overnight. The methanol is removed in vacuo and the aqueous residue is treated with 0.25M sodium hydrogen sulfate until the pH is adjusted to 3.5 (pH meter). The mixture is extracted with 4×10 ml diethyl ether. The organics are combined, dried over magnesium sulfate, and concentrated in vacuo to a yellow oil (14 mg).

The oil is chromatographed over 900 mg silica gel (230-400 mesh) eluting with 40% acetone/hexane and collecting 0.5 ml fractions. Fractions 8-28 are combined and concentrated to afford 5 mg of the title compound.

TLC (silica gel-60, F-254): $R_f = 0.18$ (50% acetone/hexane).

EXAMPLE 91

δ-Hydroxy-5-(3-hydroxy-1,5-undecadienyl)furanhexanoic acid

Sodium (bis) 2-methoxyethoxy-aluminum hydride (3.4M/toluene; 0.080 ml, 0.27 mmole) is dissolved in 1 ml toluene in an oven dried 10 ml 2-neck round bottom flask under nitrogen. The solution is cooled to $-22°$ C. and treated slowly dropwise with δ-hydroxy-5-(3-hydroxy-5-undecen-1-ynyl)-2-furanhexanoic acid, (15 mg, 0.040 mmole) in 3×0.5 ml toluene. The reaction mixture is stirred 4.5 hours at 19° to $-22°$ C., quenched with 300 μl water, and stirred vigorously with 5 ml 0.5M sodium potassium tartrate for 1 hour. The pH of the mixture is adjusted to 3.5 with 0.25M sodium hydrogen sulfate (pH meter). The mixture is extracted with 4×10 ml diethyl ether. The organics are combined, dried over magnesium sulfate, and concentrated in vacuo to provide 14 mg of a 1:1 mixture of starting material and product.

The product mixture is dissolved in 500 μl 80:20 methanol/water. The mixture is resolved in five equal injections over a 10×255μ ODS column. (245 nm, 3 ml/min, methanol/water/acetic acid; 72.7/27.3/0.1 pH=5.6 with 2M ammonium hydroxide). The pH of each pool is adjusted to 10.0 with 0.5N lithium hydroxide, the methanol removed in vacuo, and the pH readjusted to 3.5 with 0.25M sodium hydrogen sulfate (pH meter). Each pool is extracted with 4×10 ml diethyl ether. The respective organics are combined, dried over magnesium sulfate and concentrated in vacuo to provide 5 mg of the title compound and 4 mg of the title compound of Example 90.

TLC (silica gel-60, F-254): $R_f = 0.18$ (50% acetone/hexane).

EXAMPLE 92

Tetrahydro-6-[[6-(3-hydroxy-1,5-undecadienyl)-2-pyridinyl]methyl]-2H-pyran-2-ol

Sodium (bis) 2-methoxyethoxy aluminum hydride (3.4M, toluene; 200 ml, 0.675 mmole) is dissolved in 1 ml dry toluene in an oven dried 10 ml 2-neck round bottom flask under nitrogen at 0° C. 5-[6-[3-hydroxy-undec-5Z-en-1-yn-yl]pyridine-2-yl]methyl-tetrahydropyran-2-one (48 mg, 0.135 mmole), in 3×0.3 ml dry toluene, is added slowly dropwise to the reaction mixture at 0° C. The reaction is stirred at 0° C. for 3.5 hours, quenched with 200 ml water, and stirred vigorously for 30 minutes with 5 ml 0.5M sodium potassium tartrate and 5 ml diethyl ether. The reaction mixture is extracted with 4×10 ml diethyl ether. The organics are combined, dried over magnesium sulfate, and concentrated in vacuo to a pale oil (46 mg).

The oil is chromatographed over 2 g silica gel (230-400 mesh), eluting with 20% acetone/hexane and collecting 1 ml fractions. Fractions 7-20 are combined and concentrated to provide 30 mg of the title compound.

TLC (silica gel-60, F-254): $R_f = 0.51$ (50% acetone/hexane).

EXAMPLE 93

(a) 5-Bromo-2-carbonyl-furan

A flame dried 2000 ml 3-neck round bottom flask under nitrogen is charged with furfural (49.7 ml, 600 mmole) and 250 ml dichloroethane. The solution is treated successively with sulfur (10 mg, 0.312 mmole) and hydroquinone (100 mg, 0.908 mmole) at room temperature. The mixture is heated to reflux and treated slowly dropwise with bromine (38 ml, 738 mmole), in 150 ml dichloroethane. The reaction mixture is maintained at reflux until evolution of hydrobromic acid ceases (2.5 hours). The reaction is cooled to room temperature and the dichloroethane removed in vacuo. The black residue is steam distilled until 650 ml of distillate has been collected. The distillate is extracted with 4×100 ml ethyl acetate. The organics are combined, dried over magnesium sulfate, and concentrated in vacuo to give 37 g of a crude yellow solid. The crude solid is recrystallized from 95% ethanol to provide 24.5 g of the title compound.

TLC (silica gel-60, F-254): $R_f=0.32$ (30% ethyl acetate/hexane.)

(b) Methyl-6-[5-bromo-furan-2yl]-5-hexenoate

An oven dried 250 ml 3-neck round bottom flask under nitrogen is charged with sodium hydride (50% in oil; 1.32 g, 27.5 mmole). The sodium hydride is triturated with 2×5 ml pentane to remove excess mineral oil. The flask is subsequently charged with 65 ml dimethylsulfoxide and the mixture heated to 65° C. for one hour. The reaction mixture is cooled to room temperature and treated portionwise with 4-carboxybutyl-triphenyl-phoephonium bromide (6.06, 13.7 mmole). The red ylid solution is stirred 30 minutes at room temperature, cooled to 0° C., and treated slowly dropwise with 5-bromo-2-carbonyl-furan (2.00 g, 11.4 mmole) in 10 ml dimethylsulfoxide. The reaction mixture is slowly warmed to room temperature and stirred 3 hours. The mixture is subsequently treated slowly dropwise with methyl iodide (22 ml, 353 mmole) and stirred overnight. The reaction is quenched with 5 ml water and poured into 100 ml 90% saturated sodium chloride. The mixture is extracted with 4×100 ml diethyl ether. The organics are combined and washed successively with 1×100 ml saturated sodium chloride and 1×100 ml saturated sodium thiosulfate. The organics are dried over magnesium sulfate and concentrated in vacuo to a reddish oily residue.

The residue is chromatographed over 97 g silica gel (230-400 mesh) eluting with 30% ethyl acetate/hexane and collecting 22 ml fractions. Fractions 9-12 are combined and concentrated to afford 2.82 g of the title compound.

TLC (silica gel-60, F-254): $R_f=0.58$ (30% ethyl acetate/hexane.)

(c) Methyl-6-[5-bromo-furan-2yl]-5,6-epoxy-hexanoate m-Chloroperbenzoic acid (80-85%; 90 mg, 0.417 mmole) is dissolved in 1 ml dichloromethane in a 10 ml one-neck round bottom flask under nitrogen. The solution is layered with 1.5 ml saturated sodium bicarbonate and stirred vigorously. Methyl-6-[5-bromo-furan-2yl]-5-hexenoate (90 mg, 0.333 mmole), in 1 ml dichloromethane, is added rapidly to the reaction mixture at room temperature. The reaction is stirred 4 hours at room temperature. The excess m-chloroperbenzoic acid is quenched with 1 ml saturated sodium sulfite and the reaction is poured into 10 ml saturated sodium bicarbonate. The mixture is extracted with 2×10 ml diethyl ether. The organics are combined, dried over magnesium sulfate, and concentrated in vacuo to a yellow oil (101 mg).

The oil is chromatographed over 5 g silica gel (230-400 mesh), eluting with 20% ethyl acetate/hexane and collecting 1.5 ml fractions. Fractions 12-16 are combined and concentrated to afford 42 mg of the title compound.

TLC (silica gel-60, F-254): $R_f=0.30$ (30% ethyl acetate/hexane.)

(d) Methyl-6-[5-bromo-furan-2-yl]-5-hydroxy-hexanoate

Methyl-6-[5-bromo-furan-2yl]-5,6-epoxy-hexanoate (244 mg, 0.844 mmole) and sodium cyanoborohydride (80 mg, 1.27 mmole) are combined in 4 ml dry tetrahydrofuran in an oven dried 10 ml 2-neck round bottom flask under nitrogen at 0° C. The reaction mixture is treated with boron trifluoride etherate (60 μl, 0.485 mmole) slowly dropwise. The reaction mixture is quenched with 4 ml saturated sodium bicarbonate, poured into 20 ml saturated sodium chloride, and extracted with 4×10 ml diethyl ether. The organics are combined, dried over magnesium sulfate, and concentrated in vacuo to a yellow oil.

The oil is chromatographed over 18 g silica gel (230-400 mesh), eluting with 35% ethyl acetate/hexane and collecting 3 ml fractions. Fractions 26-40 are combined and concentrated to afford 164 mg of the title compound.

TLC (silica gel-60, F-254): $R_f=0.36$ (50% ethyl acetate/hexane.)

(e) 6-[5-Carbonyl-furan-2yl]-hex-5-yne-1-ol

5-Bromo-2-carbonyl-furan (2.5 g, 14.3 mmole) and 5-hexyne-1-ol (1.87 ml, 17.1 mmole) are dissolved in 35 ml degassed triethylamine in a 100 ml one-neck round bottom flask under argon. The solution is treated with (bis) triphenylphosphine palladium dichloride (301 mg, 0.429 mmole), heated to 55° C., and treated with cuprous iodide (41 mg, 0.214 mmole). The reaction mixture is stirred at 55° C. for 1.5 hours, cooled to room temperature, and the volatiles removed in vacuo. The dark residue is partitioned between 25 ml 90% saturated sodium chloride/ammonium chloride (1:1) and 25 ml diethyl ether. The layers are separated and the aqueous layer extracted with 4×25 ml diethyl ether. The organics are combined, dried over magnesium sulfate, and concentrated in vacuo to an amber oil.

The oil is chromatographed over 100 g silica gel (230-400 mesh), eluting with 65% ethyl acetate/hexane and collecting 20 ml fractions. Fractions 14-31 are combined and concentrated to afford 2.49 g of the title compound.

TLC (silica gel-60, F-254): $R_f=0.41$ (50% acetate/hexane.)

(f) 6-[5-Carbonyl-furan-2yl]-5Z-hexen-1-ol

6-[5-Carbonyl-furan-2-yl]-hex-5-yne-1-ol (724 mg, 3.77 mmole) is dissolved in 20 ml ethyl acetate in a 100 ml one-neck round bottom flask. The solution is treated successively with quinoline (one drop) and lindlar poisoned 5% palladium on calcium carbonate (75 mg). The reaction mixture is hydrogenated at atmospheric pressure until the theoretical amount of hydrogen is taken up (85 ml). The mixture is filtered through a one-inch bed of celite and the filter cake washed well with fresh ethyl acetate. The filtrate is collected and concentrated in vacuo to an amber oil.

The oil is chromatographed over 30 g silica gel (230-400 mesh), eluting with 65% ethyl acetate/hexane, and collecting 9 ml fractions. Fractions 16-23 are combined and concentrated to provide 680 mg of the title compound.

TLC (silica gel-60, F-254): $R_f=0.38$ (80% ethyl acetate/hexane.)

(g) 6-[5-(2-Chloroethylenyl)-furan-2yl]-5Z-hexen-1-ol

Chloromethyltriphenylphosphonium chloride (2.65 g, 7.72 mmole) is suspended in 18 ml dry tetrahydrofuran in an oven dried 100 ml 2-neck round bottom flask under nitrogen. The suspension is cooled to 0° C., treated slowly dropwise with butyllithium (4.78 ml, 7.41 mmole), and stirred 20 minutes at 0° C. 6-[5-Carbonylfuran-2yl]-5Z-hexen-1-ol (600 mg, 3.10 mmole), in 3×3 ml dry tetrahydrofuran, is added rapidly dropwise to the reaction mixture at 0° C. The reaction mixture is stirred 2 hours at 0° C., quenched with 5 ml saturated sodium chloride, and the bulk of the tetrahydrofuran removed in vacuo. The residue is poured into 25 ml saturated sodium chloride and extracted with 4×20 ml diethyl ether. The organics are combined, dried over magnesium sulfate, and concentrated in vacuo to a pasty yellow residue.

The residue is chromatographed over 32 g silica gel (230–400 mesh), eluting with 25% ethyl acetate/hexane, and collecting 8 ml fractions. Fractions 16–30 are combined and concentrated to provide 640 mg of the title compound.

TLC (silica gel-60, F-254): $R_f=0.25$ (30% ethyl acetate/hexane.)

(h)
1-t-Butyldimethylsilyloxy-6-[5-(2-chloroethenyl)-furan-2-yl]-5Z-hexene

6-[5-(2-Chloroethylenyl)-furan-2yl]-5Z-hexen-1-ol (163 mg, 0.722 mmole), triethylamine (175 μl, 1.25 mmole), t-butyldimethylsilyl chloride (152 mg, 1.01 mmole), and N,N-dimethylaminopyridine (9 mg, 0.072 mmole) are combined in 3 ml dry dichloromethane in a 10 ml one-neck round bottom flask under nitrogen at 0° C. The reaction mixture is stirred 30 minutes at 0° C., warmed to room temperature and stirred for one hour. The mixture is diluted with 25 ml diethyl ether, poured into 15 ml 90% saturated sodium chloride, and washed with 1×15 ml saturated sodium bicarbonate. The organics are collected, dried over magnesium sulfate, and concentrated in vacuo to a yellow oil.

The oil is chromatographed over 32 g silica gel (230-400 mesh), eluting with 8% ethyl acetate/hexane, and collecting 6 ml fractions. Fractions 6-11 are combined and concentrated to afford 226 mg of the title compound.

TLC (silica gel-60, F-254): $R_f=0.72$ (30% ethyl acetate/hexane.)

(i)
1-t-Butyldimethylsilyloxy-6-[5-ethynyl-furan-2yl]-5Z-hexene

An oven dried 25 ml 2-neck round bottom flask under nitrogen is charged with 3 ml dry tetrahydrofuran and diisopropylamine (320 μl, 2.29 mmole). The solution is cooled to 0° C., treated dropwise with butyllithium (1.3 ml, 1.99 mmole), and the mixture stirred 30 minutes at 0° C. 1-t-Butyldimethylsilyloxy-6-[5-(2-chloroethenyl)-furan-2yl]-5Z-hexene (226 mg, 0.662 mmole), in 3×0.5 ml dry tetrahydrofuran, is added dropwise to the reaction mixture at 0° C. The reaction is stirred one hour at 0° C., quenched with 1 ml sodium chloride, and poured into 10 ml saturated sodium chloride. The mixture is extracted with 4×10 ml diethyl ether. The organics are combined, dried over magnesium sulfate, and concentrated in vacuo to a dark yellow oil.

The oil is chromatographed over 10 g silica gel (230-400 mesh), eluting with 5% ethyl acetate/hexane, and collecting 3 ml fractions. Fractions 7-12 are combined and concentrated to provide 158 mg of the title compound.

TLC (silica gel-60, F-254): $R_f=0.54$ (10% ethyl acetate/hexane.)

(j)
1-t-Butyldimethylsilyloxy-6-[5-(3-hydroxy-undec-5Z-ene-1-ynyl)-furan-2-yl]-5Z-hexene 1-t-Butyldimethylsilyloxy-6-[5-ethynyl-furan-2yl]-5Z-hexene (444 mg, 1.46 mmole) is dissolved in 2 ml dry tetrahydrofuran in an oven dried 25 ml 2-neck round bottom flask under nitrogen. The solution is cooled to 0° C., treated with butyllithium (0.942 ml, 1.46 mmole), and stirred 20 minutes. The mixture is subsequently cooled to −78° C. and added slowly dropwise via cannula (N₂ pressure) to a second oven dried 25 ml 2-neck round bottom flask containing 3-nonenal (306 mg, 2.2 mmole) in 4 ml dry tetrahydrofuran at 78° C. under nitrogen. The reaction mixture is stirred 45 minutes at −78° C., warmed to 0° C., and stirred 15 minutes. The reaction is poured into 25 ml saturated sodium chloride and extracted with 4×20 ml diethyl ether. The organics are combined, dried over magnesium sulfate, and concentrated in vacuo to a yellow oil.

The oil is chromatographed over 48 g silica gel (230–400 mesh), eluting with 8% ethyl acetate/hexane, and collecting 16 ml fractions. Fractions 5–9 are combined and concentrated to provide 217 mg of 1-t-butyldimethylsilyloxy-6-[5-ethynyl-furan-2yl]-5Z-hexene. Fractions 11–17 were combined and concentrated to afford 313 mg of the title compound.

TLC (silica gel-60, F-254): $R_f=0.21$ (10% ethyl acetate/hexane.)

(k)
1-t-Butyldimethylsilyloxy-6-[5-(3-hydroxy-undec-1E,5Z-dien-1-yl)-furan-2-yl]-5Z-hexene Sodium (bis) 2-methoxyethoxy-aluminum hydride (0.58 ml, 1.65 mmole) is dissolved in 3 ml dry toluene in an oven dried 50 ml 2-neck bound bottom flask under nitrogen. The solution is cooled to −22° C. and 1-t-Butyldimethylsilyloxy-6-[5-(3-hydroxy-undec-5Z-ene-1-ynyl)-furan-2-yl]-5Z-hexene (293 mg, 0.659 mmole), in 3×1 ml dry toluene, is added dropwise. The reaction mixture is stirred 1.5 hours at −22° C., quenched with 250 μl water, and warmed to room temperature. The mixture is stirred vigorously with 10 ml 0.5M sodium potassium tartrate and 10 ml diethyl ether for one hour. The reaction is poured into 10 ml saturated sodium chloride and extracted with 4×10 ml diethyl ether. The organics are combined, dried over magnesium sulfate, and concentrated in vacuo to a pale yellow oil.

The oil is chromatographed over 15 g silica gel (230–400 mesh), eluting with 8% ethyl acetate/hexane, and collecting 3 ml fractions. Fractions 16–27 are combined and concentrated to afford 250 mg of the title compound.

TLC (silica gel-60, F-254): $R_f=0.55$ (30% ethyl acetate/hexane.)

(l)
Methyl-6-[5-(3-Hydroxy-undec-5Z-ene-1-ynyl)-furan-2-yl]-5-hexenoate

3-Hydroxyundec-5Z-ene-1-yne (335 mg, 2.02 mmole) and methyl-6-[5-bromo-furan-2yl]-5-hexenoate (491 mg, 1.79 mmole) are combined in 4 ml degassed triethylamine in a 10 ml one-neck round bottom flask under argon. The solution is treated with (b) triphenylphoephine palladium dichloride (42 mg, 0.060 mmole), heated to 80° C., and treated with cuprous iodide (6 mg, 0.030 mmole). The reaction mixture is stirred 1.5 hours at 80° C., cooled to room temperature, and the volatiles removed in vacuo. The black residue is partitioned between 10 ml saturated sodium chloride/ammonium chloride (1:1) and 10 ml diethyl ether. The aqueous layer is extracted with 3×10 ml diethyl ether. The organics are combined, dried over magnesium sulfate, and concentrated in vacuo to a black oil (753 mg).

The oil is chromatographed over 52 g silica gel (230–400 mesh), eluting with 18% ethyl acetate/hexane, and collecting 8 ml fractions. Fractions 26–45 are combined and concentrated to afford 450 mg of the title compound.

TLC (silica gel-60, F-254): $R_f = 0.40$ (30% ethyl acetate/hexane).

(m)
6-[5-(3-Hydroxy-undec-5Z-ene-1-ynyl)-furan-2-yl]-5-hexenoic acid

Methyl-6-[5-(3-Hydroxy-undec-5Z-ene-1-ynyl)-furan-2-yl]-5-hexenoate (232 mg, 0.649 mmole) is dissolved in 15 ml methanol in a 100 ml one-neck round bottom flask. The solution is treated with 0.5N sodium hydroxide (5 ml, 2.5 mmole) and the reaction mixture stirred for 2 hours at room temperature. The methanol is removed in vacuo and the pH of the aqueous residue is adjusted to 3.5 with 0.25M sodium hydrogen sulfate (pH meter). The mixture is extracted with 4×10 ml diethyl ether. The organics are combined, dried over magnesium sulfate, and concentrated to an amber oil (230 mg).

The oil is chromatographed over 11 g silical gel (230–400 mesh), eluting with 35% acetone/hexane, and collecting 3 ml fractions. Fractions 11–36 are combined and concentrated to afford 170 mg of the title compound.

TLC (silica gel-60, F-254): $R_f = 0.38$ (50% acetone/hexane).

(n)
Methyl-6-[5-(3-Hydroxy-undec-1E,5Z-dien-1-yl)-furan-2-yl]-5-hexenoate

Sodium (bis) 2-methoxyethoxy-aluminum hydride (0.29 ml, 0.987 mmole) is dissolved in 2 ml dry toluene in an oven dried 25 ml 2-neck round bottom flask under nitrogen. The solution is cooled to −22° C. and treated slowly dropwise with 6-[5-(3-hydroxy-undec-5Z-ene-1-ynyl)-furan-2-yl]-5-hexenoic acid (100 mg, 0.290 mmole) in 3×0.5 ml toluene. The reaction mixture is stirred 1.5 hours at −22° C., quenched with 300 μl water, and stirred vigorously with 10 ml 0.5M sodium potassium tartrate. The pH of the mixture is adjusted to 3.5 with 0.25M sodium hydrogen sulfate (pH meter) and the mixture extracted with 4×10 ml diethyl ether. The organics are combined, washed with 1×10 ml saturated sodium chloride, and dried over magnesium sulfate. The organics are concentrated in vacuo to provide 96 mg of an amber oil consisting of a 2:1:2 mixture of 1-[5-(6-hydroxy-1-hexenyl)-2-furanyl]-1,5-undecadien-3-ol (Z,E,Z) and the desired 12-trans allylic alcohol-acid. The crude mixture is dissolved in 3 ml diethyl ether and treated with ethereal diazomethane at 0° C. The reaction mixture is concentrated in vacuo and the residue is redissolved in 20 ml diethyl ether. The organics are washed successively with 1×20 ml 5% hydrochloric acid and 1×20 ml saturated sodium bicarbonate. The organics are dried over magnesium sulfate and concentrated in vacuo too a crude yellow oil (99 mg).

The oil is chromatographed over 7 g silica gel (230–400 mesh), eluting with 25% ethyl acetate/hexane and collecting 3 ml fractions. Fractions 7–11 are combined and concentrated to provide 52 mg of a 1:1 mixture of the title compound/propargylic alcohol ester of (1) above.

The ester mixture is dissolved in 1.0 ml 8% ethyl acetate/hexane and separated over a 10×25 cm 5μ Ultrasphere column in 12 equal injections (7.5% ethyl acetate/hexane, 3 ml/mn, 270 nm). The chromatography results in the isolation of 23 mg (22%) of propargylic alcohol-ester of (1) above, 12 mg (11%) of the allylic alcohol-5,6 cis olefin-ester, and 2 mg (2%) of the allylic alcohol-5,6 trans olefin-ester as colorless oils.

TLC (silica gel-60, F-254): $R_f = 0.65$ (50% acetone/hexane).

(o)
Methyl-5-hydroxy-6-[5-(3-hydroxy-undec-5Z-ene-1-ynyl)-furan-2-yl]-hexanoate

Methyl-6-[5-bromo-furan-2-yl]-5-hydroxy-hexanoate (164 mg, 0.563 mmole) and 3-hydroxy-undec-5Z-ene-1-yne (120 mg, 0.722 mmole) are combined in 2 ml degassed triethylamine in a 25 ml one-neck round bottom flask under argon. The mixture is warmed to 50° C., treated with (bis) triphenylphosphine palladium dichloride (20 ml), 0.031 mmole), and warmed to 80° C. The reaction mixture is treated with cuprous iodide (3 mg, 0.015 mmole) and stirred at 80° C. for 2 hours. The mixture is cooled to room temperature and the volatiles removed in vacuo. The black residue is partitioned between 10 ml saturated sodium chloride and 10 ml diethyl ether. The aqueous layer is extracted with 3×10 ml diethyl ether. The organics are combined, dried over magnesium sulfate, and concentrated in vacuo to a black oil.

The oil is chromatographed over 18 g silica gel (230–400 mesh), eluting with 35% ethyl acetate/hexane, and collecting 3 ml fractions. Fractions 38–48 are combined and concentrated to afford 100 mg of the title compound.

TLC (silica gel-60, F-254): $R_f = 0.52$ (50% acetone/hexane).

(p)
5-Hydroxy-6-[5-(3-hydroxy-undec-5Z-ene-1-ynyl)-furan-2-yl]-hexanoic acid

Methyl-5-hydroxy-6-[5-(3-hydroxy-undec-5Z-ene-1-ynyl)-furan-2-yl]-hexanoate (15 mg, 0.040 mmole) is dissolved in 1.6 ml methanol in a 10 ml one-neck round bottom flask under nitrogen. The solution is treated with 0.5N sodium hydroxide (0.8 ml, 0.40 mmole) and the reaction mixture is stirred overnight. The methanol is removed in vacuo and the aqueous residue is treated with 0.25M sodium hydrogen sulfate until the pH is adjusted to 3.5 (pH meter). The mixture is extracted with 4×10 ml diethyl ether. The organics are combined, dried over magnesium sulfate, and concentrated in vacuo to a yellow oil (14 mg).

The oil is chromatographed over 900 mg silica gel (230–400 mesh), eluting with 40% acetone/hexane and collecting 0.5 ml fractions. Fractions 8–28 are combined and concentrated to afford 5 mg of the title compound.

TLC (silica gel-60, F-254): $R_f = 0.18$ (50% acetone/hexane).

CHART A
Preparation of some compounds of Formula I and compounds of Formula II:
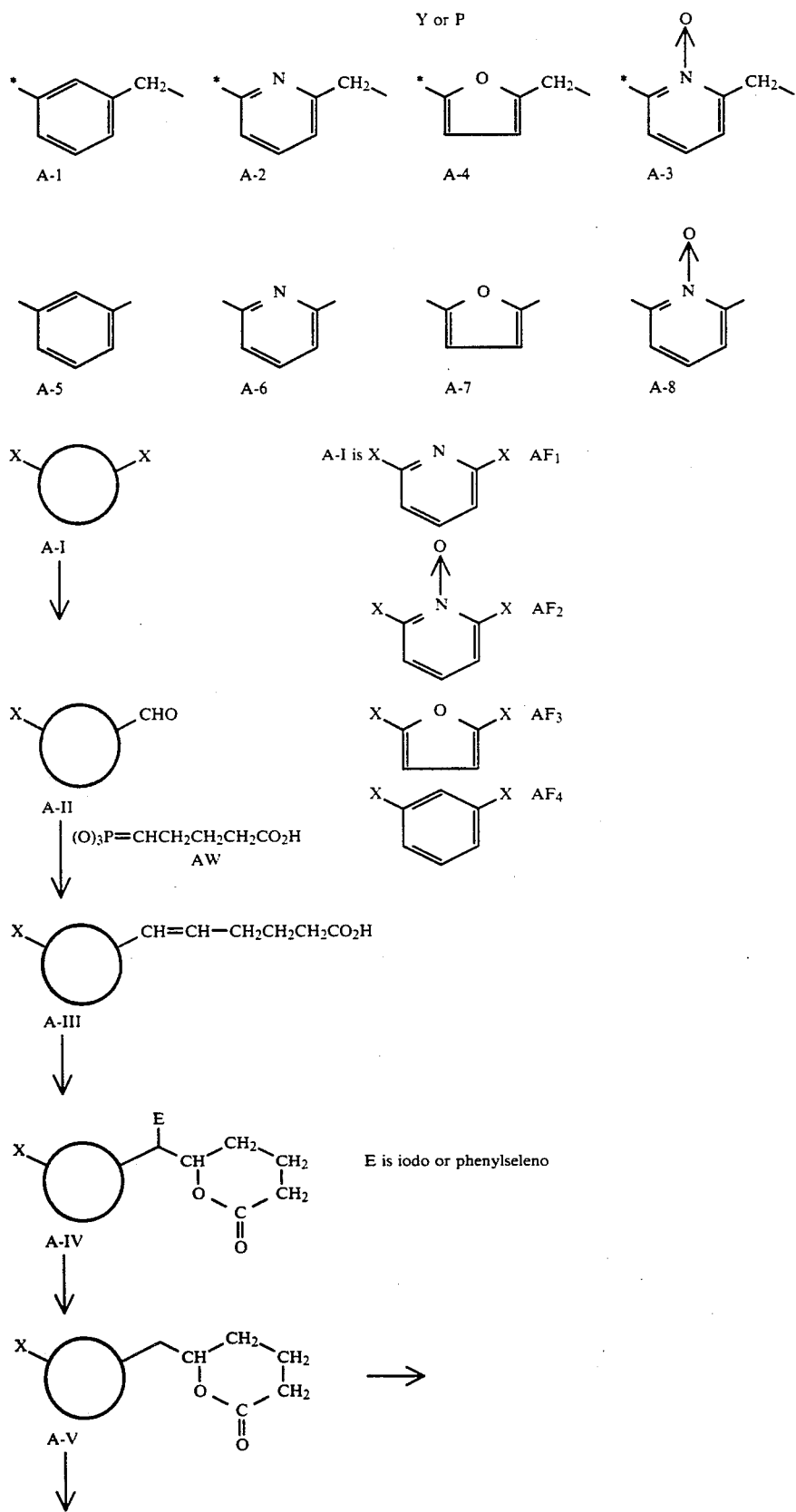

-continued
CHART A
Preparation of some compounds of Formula I and compounds of Formula II:
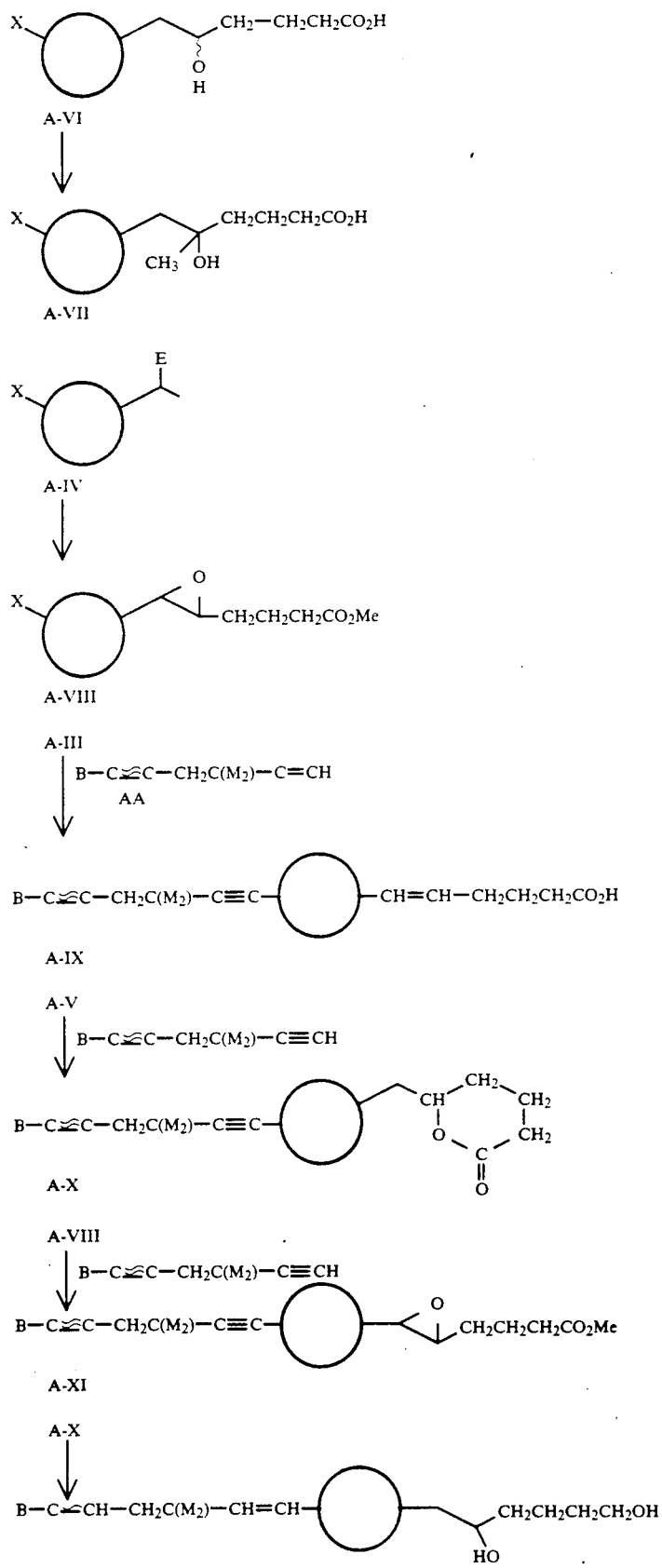

-continued
CHART A
Preparation of some compounds of Formula I and compounds of Formula II:

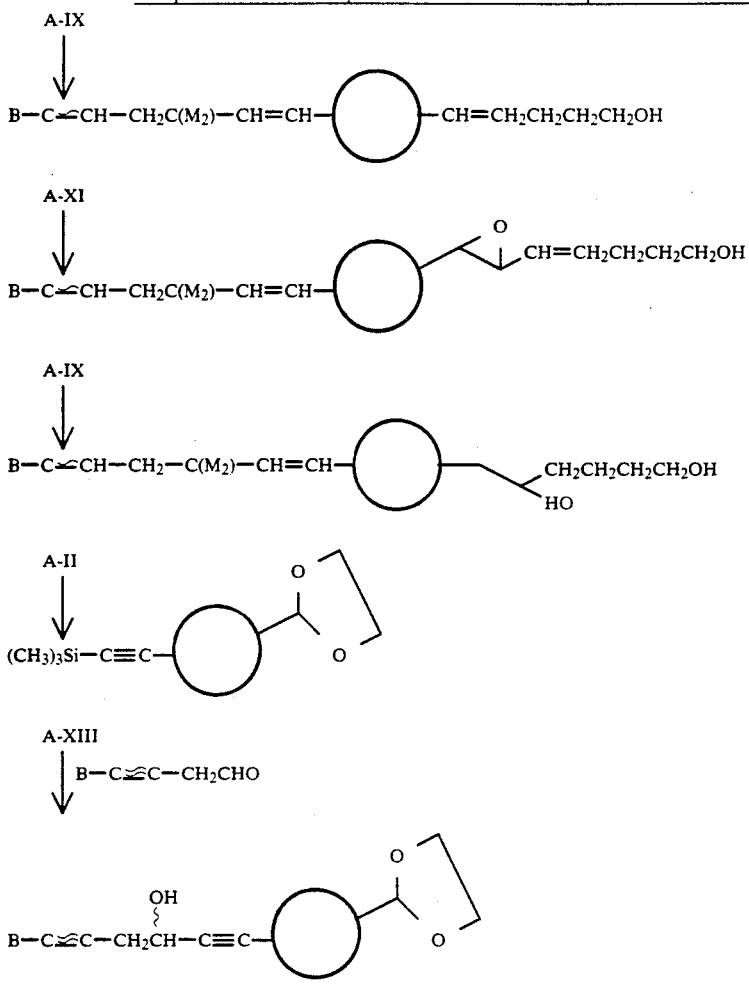

I claim:
1. A compound of the formula

wherein —C≊C— is —CH$_2$CH$_2$—, cis or trans —CH=CH—, or C≡C—;
wherein P is

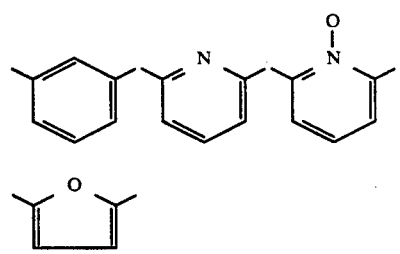

wherein Q is
(a) —CH$_2$—CR(OH)—(CH$_2$)$_3$—Z,
(b) —CH$_2$—Z$_1$,
(c) —R$_5$—(CH$_2$)$_3$—Z, or
(d) —CR(OH)—Z$_1$;
wherein Z is (a) —COOH,
(b) —COO(C$_1$-C$_{12}$ alkyl),
(c) —COO(C$_3$-C$_{10}$ cycloalkyl),
(d) —CH$_2$OH, or
(e) —CH$_3$;
wherein B is (C$_4$-C$_7$) cycloalkyl, —(CH$_2$)$_a$—CH$_2$OH or —CR$_3$R$_4$—(CH$_2$)$_a$—CH$_3$;
wherein a is zero or an integer of 1 to 5 and R$_3$ and R$_4$ are the same or different and are H, F or CH$_3$, with the proviso that CR$_3$R$_4$ is not CFCH$_3$;
wherein R$_5$ is
(a) cis—CH=CH—,
(b) trans—CH=CH—,
(c) —C≡C—,
(d) —CR(OH)—CR(OH)—,
(e) —CH(SL$_7$)—CR(OH)—, or
(f)

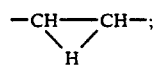

wherein each R is H or CH$_3$;
wherein Z$_1$ is a 5 or 6-membered lactone or lactol; and
wherein L$_7$ is (a) —(CH$_2$)$_2$COOH,
(b) —CH$_2$COOH,
(c) —CH$_2$CH(NH$_2$)COOH,
(d) —CH$_2$—CH(CONHCH$_2$COOH)—NH—CO—CH$_2$CH$_2$—CH(COOH)—NH$_2$, or
(e) —CH$_2$CH(NH$_2$)CONHCH$_2$COOH.

2. A compound of claim 1, wherein Q is —CH$_2$—Z$_1$ or —CH$_2$—CR(OH)—(CH$_2$)$_3$—Z.

3. A compound of claim 2, wherein Q is —CH$_2$—CHOH—(CH$_2$)$_3$—Z; Z is —CH$_2$OH or —COOH; and B is —(CH$_2$)$_4$—CH$_3$ or —(CH$_2$)$_4$—CH$_2$OH.

4. A compound of claim 1, wherein Q is —R$_5$—(CH$_2$)$_3$—Z or —CR(OH)—Z$_1$.

5. A compound of claim 4, wherein Q is —CH=CH—(CH$_2$)$_3$—Z, and Z and B are as defined in claim 3.

6. A compound of claim 4, wherein Q is

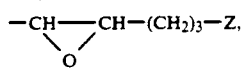

and Z and B are as defined in claim 3.

7. A compound of claim 2, selected from
6-[3-(3-hydroxy-1,5-undecadienyl)phenyl]-1,5-hexanediol;
tetrahydro-6-[[3-(3-hydroxy-5-undecen-1-ynyl)phenyl]methyl]-2H-pyran-2-one;
δ-hydroxy-3-(3-hydroxy-5-undecen-1-ynyl)-benzenehexanoic acid;
tetrahydro-6-[[3-(3-hydroxy-1,5-undecadienyl)phenyl]methyl]-2H-2-one;
δ-hydroxy-3-(3-hydroxy-1,5-undecadienyl)-benzenehexanoic acid;
tetrahydro-6-[[6-(3-hydroxy-5-undecen-1-ynyl)-2-pyridinyl]methyl]-2H-pyran-2-one;
δ-hydroxy-6-(3-hydroxy-5-undecen-1-ynyl)-2-pyridinehexanoic acid;
δ-hydroxy-6-(3-hydroxy-1,5-undecadienyl)-2-pyridinehexanoic acid;
tetrahydro-6-[[6-(3-hydroxy-1,5-undecadienyl)-2-pyridinyl]methyl]-2H-pyran-2-ol;
(E,Z)-6-[5-(3-hydroxy-1,5-undecadienyl)-2-furanyl]-1,5-hexanediol;
δ-hydroxy-5-(3-hydroxy-5-undecen-1-ynyl)-2-furanehexanoic acid;
δ-hydroxy-5-(3-hydroxy-1,5-undecadienyl)-2-furanehexanoic acid;
6-[6-(3-hydroxy-5-undecenyl)-2-pyridinyl]-1,5-hexanediol;
tetrahydro-6-[[6-(3-hydroxy-1,5-undecadienyl)-2-pyridinyl]methyl]-2H-pyran-2-one; and
6-[6-(3-hydroxy-1-undecenyl)-2-pyridinyl]-1,5-hexanediol.

8. A compound of claim 4, selected from
(E,Z,Z)-6-[3-(3-hydroxy-1,5-undecadienyl)phenyl]-5-hexenoic acid;
3-[3-(3-hydroxy-1,5-undecadienyl)phenyl]-oxiranebutanoic acid;
3-[3-(3-hydroxy-1,5-undecadienyl)phenyl]-oxiranebutanol;
(E,Z,Z)-6-[6-(3-hydroxy-1,5-undecadienyl)-2-pyridinyl]-5-hexenoic acid;
(E,Z,Z)-6-[3-(3-hydroxy-1,5-undecadienyl)phenyl]-5-hexenoic acid;
(E,Z,Z)-1-[6-(6-hydroxy-1-hexenyl)-2-pyridinyl]-1,5-undecadien-3-ol;
(Z,Z)-6-[6-(3-hydroxy-5-undecen-1-ynyl)-2-pyridinyl]-5-hexenoic acid;
3-[6-(3-hydroxy-1,5-undecadienyl)-2-pyridinyl]-oxiranebutanoic acid;
3-[6-(3-hydroxy-1,5-undecadienyl)-2-pyridinyl]-oxiranebutanol;
(E,Z,Z)-1-[6-(6-hydroxy-1-hexenyl)-2-pyridinyl]-1,5-undecadien-3R-ol;
(E,Z,Z)-1-[6-(6-hydroxy-1-hexenyl)-2-pyridinyl]-1,5-undecadien-3S-ol;
(Z,E,Z)-1-[5-(6-hydroxy-1-hexenyl)-2-furanyl]-1,5-undecadien-3-ol;
(Z,Z)-1-[5-(6-hydroxy-1-hexenyl)-2-furanyl]-5-undecen-1-yn-3-ol;
6-[(2-carboxyethyl)thio]-δ-hydroxy-3-(3-hydroxy-1,5-undecadienyl)benzenehexanoic acid;
(E,Z,E)-6-[5-(3-hydroxy-1,5-undecadienyl)-2-furanyl]-5-hexenoic acid;
(E,Z,Z)-6-[5-(3-hydroxy-1,5-undecadienyl)-2-furanyl]-5-hexenoic acid;
(E,Z,Z)-1-[6-(6-hydroxy-1-hexenyl)-2-pyridinyl]-1,5-undecadien-3-ol;
(E,Z,E)-6-[6-(3-hydroxy-1,5-undecadienyl)-2-pyridinyl]-5-hexenoic acid;
3-[[2,6-dihydroxy-1-[3-(3-hydroxy-1,5-undecadienyl)phenyl]hexyl]thio]propanoic acid;
N-[S-[2,6-dihydroxy-1-[3-(3-hydroxy-1,5-undecadienyl)phenyl]hexyl]-N-(trifluoroacetyl)-L-cysteinyl]-glycine methyl ester;
N-[S-[2,6-dihydroxy-1-[3-(3-hydroxy-1,5-undecadienyl)phenyl]hexyl]-L-cysteinyl]-glycine;
N-[S-[5-carboxy-2-hydroxy-1-[3-(3-hydroxy-1,5-undecadienyl)phenyl]pentyl]-L-cysteinyl]-glycine disodium salt;
[R-(E,Z,Z)]-1-[6-(6-hydroxy-1-hexenyl)-2-pyridinyl]-1,5-undecadien-3-ol;
[S-(E,Z,Z)]-1-[6-(6-hydroxy-1-hexenyl)-2-pyridinyl]-1,5-undecadien-3-ol;
3-[6-(3-hydroxy-1,5-undecadienyl)-2-pyridinyl]-oxiranebutanol;
3-[6-(3-hydroxy-1-undecynyl)-2-pyridinyl]-oxiranebutanol;
(Z)-1-[6-(6-hydroxy-1-hexenyl)-2-pyridinyl]-1-undecyn-3-ol;
(E,Z)-1-[6-(6-hydroxy-1-hexenyl)-2-pyridinyl]-1-undecen-3-ol;
3-[6-(3-hydroxy-1-undecenyl)-2-pyridinyl]-oxiranebutanol;
(E,Z,Z)-1-[6-(1-hexenyl)-2-pyridinyl]-1,5-undecadien-3-ol; and
1-[6-(3-butyloxiranyl)-2-pyridinyl]-1,5-undecadien-3-ol.

* * * * *